(12) United States Patent
Islava

(10) Patent No.: US 10,874,816 B2
(45) Date of Patent: *Dec. 29, 2020

(54) NEBULIZER APPARATUS

(71) Applicant: Care 2 Innovations, Inc., Newport Beach, CA (US)

(72) Inventor: Steve Islava, Newport Beach, CA (US)

(*) Notice: Subject to any disclaimer, the term of this patent is extended or adjusted under 35 U.S.C. 154(b) by 190 days.

This patent is subject to a terminal disclaimer.

(21) Appl. No.: 15/952,651

(22) Filed: Apr. 13, 2018

(65) Prior Publication Data

US 2018/0228993 A1 Aug. 16, 2018

Related U.S. Application Data

(60) Division of application No. 14/696,184, filed on Apr. 24, 2015, now Pat. No. 10,022,514, which is a continuation-in-part of application No. 14/658,914, filed on Mar. 16, 2015, now abandoned.

(51) Int. Cl.

| | |
|---|---|
| *A61M 16/08* | (2006.01) |
| *A61M 11/02* | (2006.01) |
| *A61M 16/14* | (2006.01) |
| *A61M 16/00* | (2006.01) |
| *A61M 11/06* | (2006.01) |
| *A61M 16/04* | (2006.01) |
| *A61M 16/06* | (2006.01) |

(52) U.S. Cl.
CPC ........ *A61M 16/0875* (2013.01); *A61M 11/02* (2013.01); *A61M 11/06* (2013.01); *A61M 16/0078* (2013.01); *A61M 16/0084* (2014.02); *A61M 16/0497* (2013.01); *A61M 16/06* (2013.01); *A61M 16/0825* (2014.02); *A61M 16/0833* (2014.02); *A61M 16/14* (2013.01); *A61M 16/0605* (2014.02); *A61M 16/0683* (2013.01)

(58) Field of Classification Search
CPC ...... A61M 11/00; A61M 11/02; A61M 11/06; A61M 16/00; A61M 16/0497; A61M 16/0816; A61M 16/0825; A61M 16/0833; A61M 16/14
USPC ............ 128/200.14, 200.21, 200.24, 203.12, 128/203.15, 203.16
See application file for complete search history.

(56) References Cited

U.S. PATENT DOCUMENTS

| | | |
|---|---|---|
| 4,094,317 A | 6/1978 | Wasnich |
| 4,456,179 A | 6/1984 | Kremer |
| 5,388,571 A | 2/1995 | Roberts |

(Continued)

OTHER PUBLICATIONS

"Care2 Medical Continuous Care Nebulizer" published online at https://www.youtube.com/watch?v=1mcdazRGtj4 by care2medical on Aug. 26, 2009 (Year: 2009).*

*Primary Examiner* — Joseph D. Boecker
(74) *Attorney, Agent, or Firm* — Marcus C. Dawes

(57) ABSTRACT

A collapsible joint for use with a nebulizer includes a housing connected to the source of carrier gas flow, an extensible and flexible airway and an extension connected to a patient applicator. A swivel joint for use with a nebulizer includes a swivel housing, a rotating airway pivoted in the swivel housing about a first axis of rotation; and an airway base coupling coupled to the swivel housing rotatable with respect to the swivel housing about a second axis of rotation. The first and second axes of rotation are mutually orthogonal at least in part to each other.

11 Claims, 22 Drawing Sheets

(56) References Cited

U.S. PATENT DOCUMENTS

| | | | |
|---|---|---|---|
| 8,042,536 B1 * | 10/2011 | Howey | A61M 11/06 128/200.14 |
| 9,566,399 B1 * | 2/2017 | Bono | A61M 11/002 |
| 10,022,514 B2 * | 7/2018 | Islava | A61M 16/0084 |
| 2002/0020409 A1 * | 2/2002 | Kidwell | A61M 16/20 128/200.14 |
| 2003/0150445 A1 | 8/2003 | Power | |
| 2005/0092325 A1 * | 5/2005 | Dionne | A61M 16/0875 128/205.25 |
| 2014/0166010 A1 | 6/2014 | Varga | |

* cited by examiner

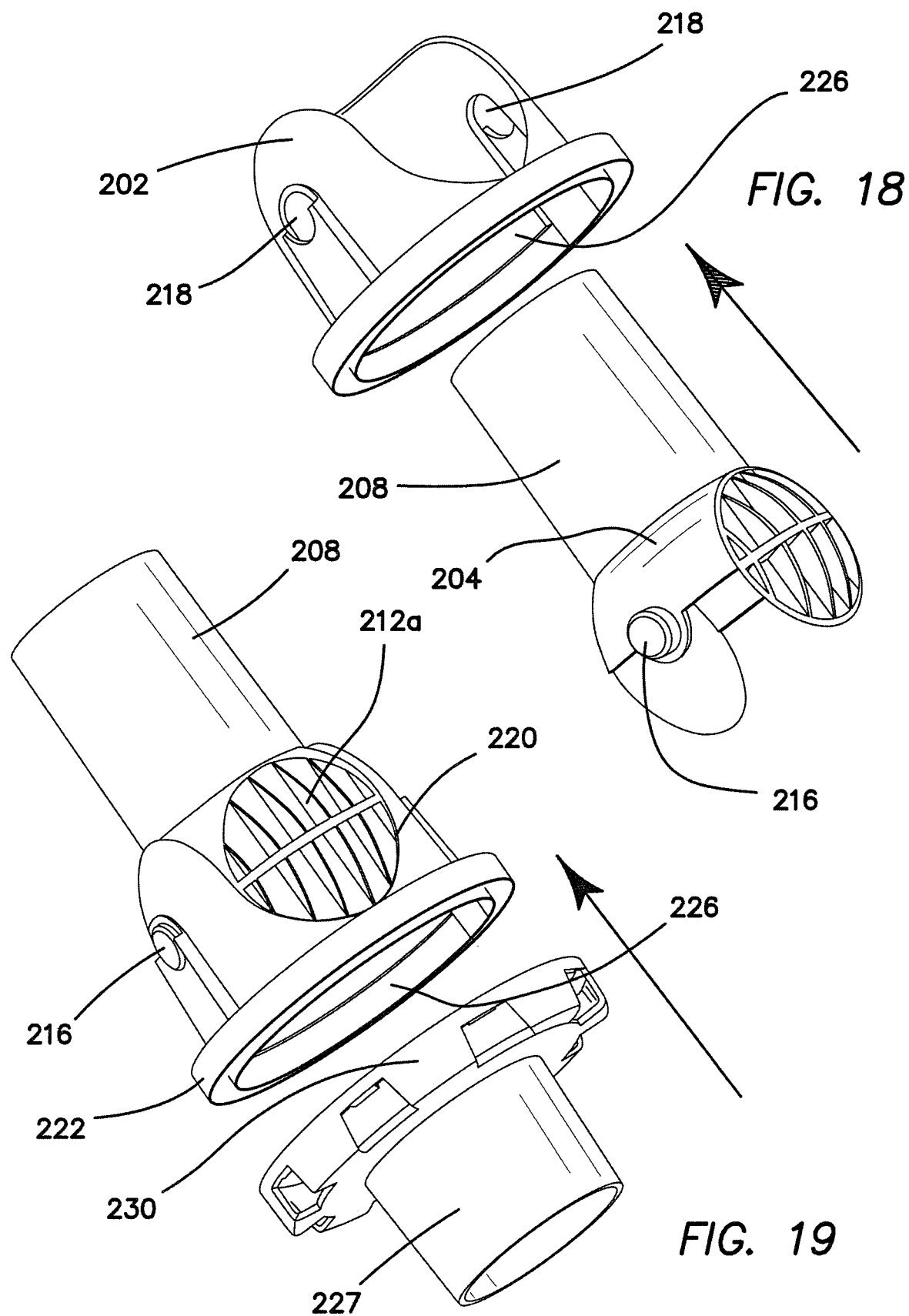

NEBULIZER APPARATUS

RELATED APPLICATIONS

This application is a divisional of U.S. patent application Ser. No. 14/696,184, filed on Apr. 24, 2015, which itself a continuation in part of U.S. patent application Ser. No. 14/658,914, filed on Mar. 16, 2015.

FIELD OF THE TECHNOLOGY

The invention relates generally to devices used in respiratory therapy, specifically to an improved apparatus for delivering a continuous dosage of aerosol medication to a patient.

DESCRIPTION OF THE PRIOR ART

Nebulizers are well known in the art, and are designed to deliver an aerosol of medication to the respiratory tract of a patient. A nebulizer apparatus is composed of a medication reservoir, a face attachment, and hosing to connect the components of the nebulizer to a carrier gas source, such as an oxygen tank, a respirator, resuscitator bag, or other pump. During operation, the nebulizer creates a flow of oxygen that intermixes with the liquid medication held in the medication reservoir. The intermixing of medication and oxygen forms an aerosol of oxygen and the medication, which is delivered to the lungs of the patient through a face attachment, such as a face mask.

Nebulizers have been utilized for treating various respiratory ailments ranging from common colds to severe asthma and complex infections of the bronchial system. Certain respiratory ailments can be more effectively treated by the delivery of medication to the patient as an aerosol, as opposed to taking the medication orally or through intravenous administration. The uses of nebulizer apparatus are not limited to respiratory ailments; they may also be used in the treatment of coronary sclerosis, coronary thrombosis and other ailments. An advantage of using a nebulizer apparatus to treat these ailments is that medicated aerosol may be carried deep into the patient's lungs. In addition, the air transmitted to the patient through the nebulizer may be humidified, or heated.

Moreover, the treatment of medical conditions using nebulizers is not limited to hospitals or other treatment centers. In addition to stationary devices, devices to heavy or bulky to be transported, nebulizers may also take the form of portable devices. Paramedic emergency medical technicians ("EMT-P") frequently use nebulizers to administer albuterol and other medications in the field, or in transit, during an emergency medical response.

There are, however, problems that interfere with the efficacy of nebulizer systems currently known in the art. These problems are particularly acute in the context of emergency medical situations in which patients are treated in the field or in transit to a hospital or other treatment center. One such problem with existing nebulizer systems, is the need to disassemble the nebulizer in order to add a medication dose to the nebulizer's medication reservoir. While in the field, or in transit, the disassembly of the nebulizer apparatus requires an EMT-P or other emergency responder to divert their attention from the emergency medical situation. The disassembly of the nebulizer apparatus to add medication may also take time that may be critical for other required emergency treatment of the patient.

The method of adding medication to the medication reservoir of a prior art nebulizer apparatus has a number of highly undesirable aspects. A patient requiring ventilation and treatment via an aerosol medication, as in the case of a severe asthma attack, is gravely ill. The interruption of oxygen delivery to a patient during an emergency, or other serious condition, can be life threatening. Moreover, the disconnection of the medication reservoir during an emergency response or other treatment can result in spillage of the liquid medication, and increased risk of contamination and infection.

Another problem with existing nebulizer systems is that spillage of medication from the medication reservoir frequently occurs during field treatment of a patient or during the transport of a patient to a treatment center. Patients often must be treated in a variety of positions, such as on their backs, sides, stomachs, or sitting upright. Many prior art medication reservoirs are not adapted to be variably positioned, and spillage of medication from the reservoir will occur unless the device (and the patient) are maintained in an upright position. Moreover, treatment often occurs in transit to a treatment center, where the patient is subject to various vibrations and motion associated with automobile travel. This vibration and motion makes it difficult to disassemble the medication reservoir and add medication without causing spillage.

What is needed therefore is a nebulizer apparatus which may be used in a variety of patient specific situations, including where the patient requires a traditional mouth piece and/or a exhaust collector.

BRIEF SUMMARY

The illustrated embodiments of the invention include a collapsible joint for use with a nebulizer apparatus for use with a source of carrier gas flow for providing aerosolized medication to a patient. The collapsible joint includes a housing defining a chamber having a top and bottom portion; a collapsible airway having two opposing ends, a first one of the two opposing ends communicating with the top portion of the chamber defined in the housing; and an extension communicating with a second one of the two opposing ends of the collapsible airway, where the extension communicates the collapsible airway with at least a portion of the nebulizer apparatus for providing aerosolized medication to the patient and where the housing communicates with the source of carrier gas flow.

One of the advantages of the illustrated embodiments is that the joint will allow the aerosolized medication to be delivered from the nebulizer to the patient, even when the patient is not standing or sitting in an upright posture. For example, the joint will facilitate administration of the aerosolized medication from the nebulizer to the patient, even when the patient is lying down or inclined.

The collapsible airway is provided with a bellows formed wall composed of flexible material which allows longitudinal extension and allows bending in any radial direction without any substantial tendency to return to an original configuration.

The bellows formed wall comprises of plurality of frustoconical sections formed in alternated orientation to provide an accordion pleated cylindrical airway.

The collapsible joint is for use with a medication reservoir for containing liquid medication having a carrier gas input to deliver pressurized gas to form aerosolized medication from the liquid medication, and further includes a rapid injection port defined in the housing for adding and replenishing medication to the medication reservoir without interrupting formation or delivery of the aerosol.

The collapsible joint further includes a swivel retainer engaging the second one of the two opposing ends of the collapsible airway and coupling with the portion of the nebulizer apparatus for providing aerosolized medication to the patient to allow rotation of the collapsible airway relative to the portion of the nebulizer apparatus for providing aerosolized medication to the patient.

The swivel retainer rotatably engages the second one of the two opposing ends of the collapsible airway. In the preferred embodiment the swivel retainer rotatably engages the portion of the nebulizer apparatus for providing aerosolized medication to the patient.

In another embodiment the swivel joint is for use with a nebulizer apparatus for use with a source of carrier gas flow for providing aerosolized medication to a patient. The swivel joint includes a swivel housing; a rotating airway pivoted in the swivel housing about a first axis of rotation; and an airway base coupling coupled to the swivel housing rotatable with respect to the swivel housing about a second axis of rotation, the first and second axes of rotation being mutually orthogonal at least in part to each other.

The swivel housing has a U-shaped opening defined therein allowing the rotating airway to be rotated about its first axis by a selective amount from a vertical orientation to a horizontal orientation.

The swivel joint further includes a rapid injection port defined in the airway base coupling for adding and replenishing medication to the nebulizer apparatus without interrupting formation or delivery of the aerosolized medication.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 18 is a partially exploded view of the rotating airway and swivel hosing portions of the nebulizer apparatus seen in FIG. 14.

FIG. 19 is a partially exploded view of the rotating airway, swivel housing, and base coupling portions of the nebulizer apparatus seen in FIG. 14.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
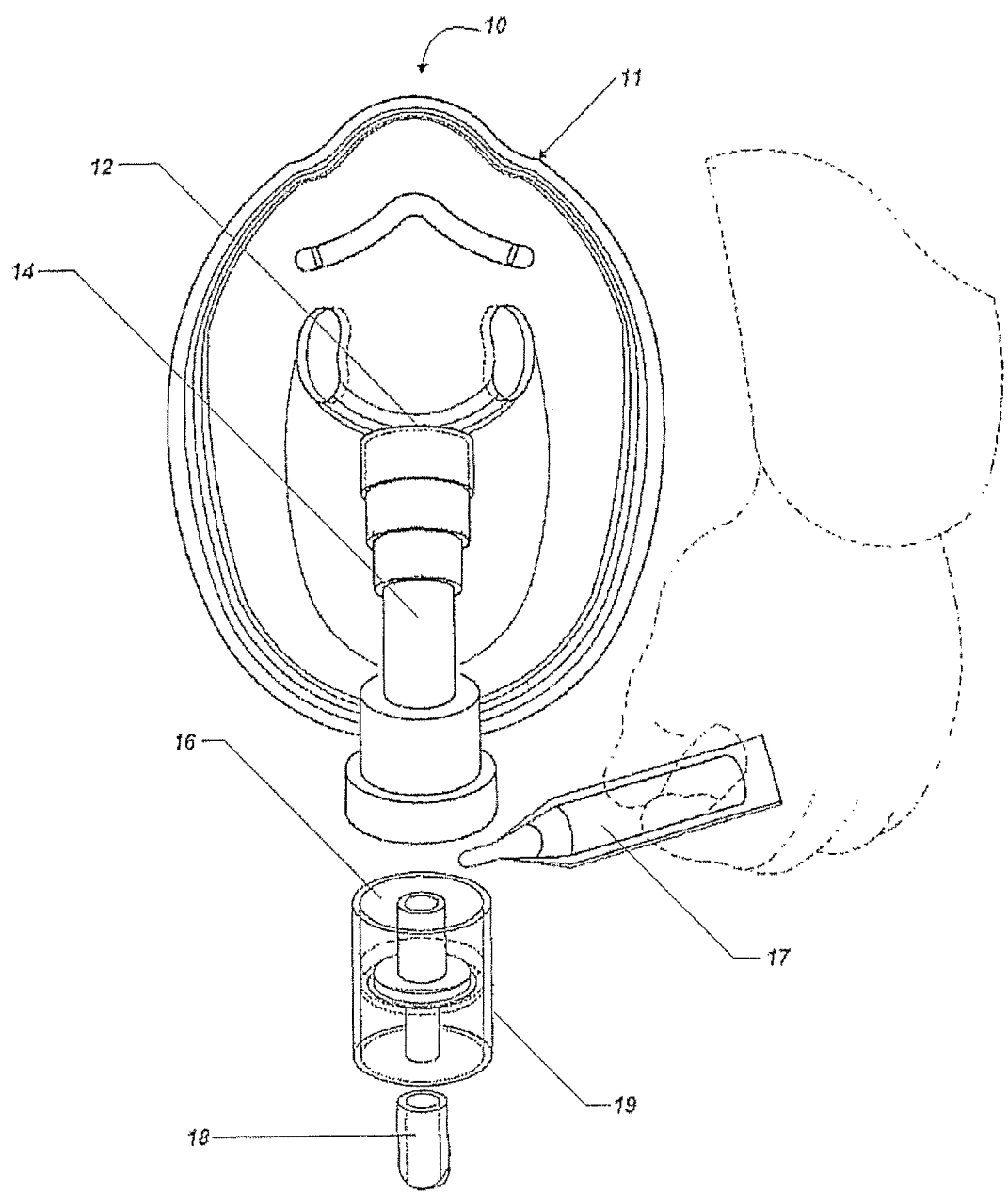
FIG. 1 is a front view of a prior art nebulizer apparatus, having a face mask and a medication reservoir. The illustration includes a representation of how the medication reservoir is filled.

Referring to FIG. 1, a prior art nebulizer apparatus 10 is represented. The apparatus is composed of a face mask 11, medication reservoir 40 and hosing 18 from the carrier gas source. The liquid medication in the medication reservoir 40 is aerosolized by the flow of carrier gas (usually oxygen) through the medication reservoir 40. The resulting aerosol flows through a hollow plastic housing 14 connecting the medication reservoir 40 to the face mask 11 of the nebulizer apparatus 10, and out of an outlet 12 for delivery to the patient.

In order to add medication to the medication reservoir of the prior art nebulizer apparatus 10, the medication reservoir 40 must be disconnected from the plastic housing 14, and the gas source must be shut down. Once the medication reservoir is disconnected, medication may be added to the opening of the medication reservoir 16 through a standard needle and syringe, needleless syringe, or other dispenser 17. During the disconnection of the medication reservoir, the ventilation circuit from the respirator, bag resuscitator or nebulizer to the patient is necessarily interrupted with possible harm to the patient.

Figure 2:
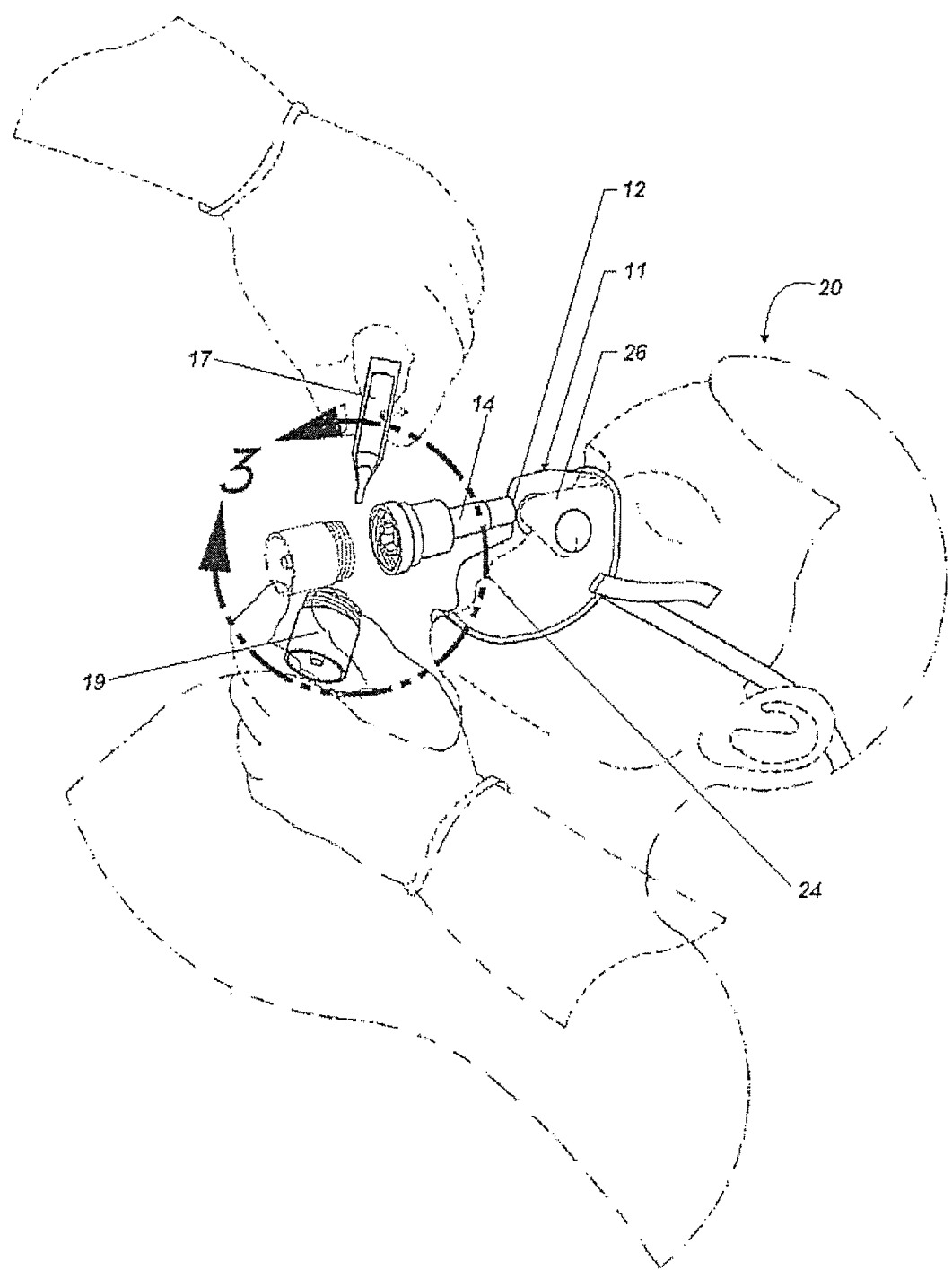
FIG. 2 is a side view of a prior art nebulizer apparatus being used for a patient lying on their back or at an angle.
Figure 3:
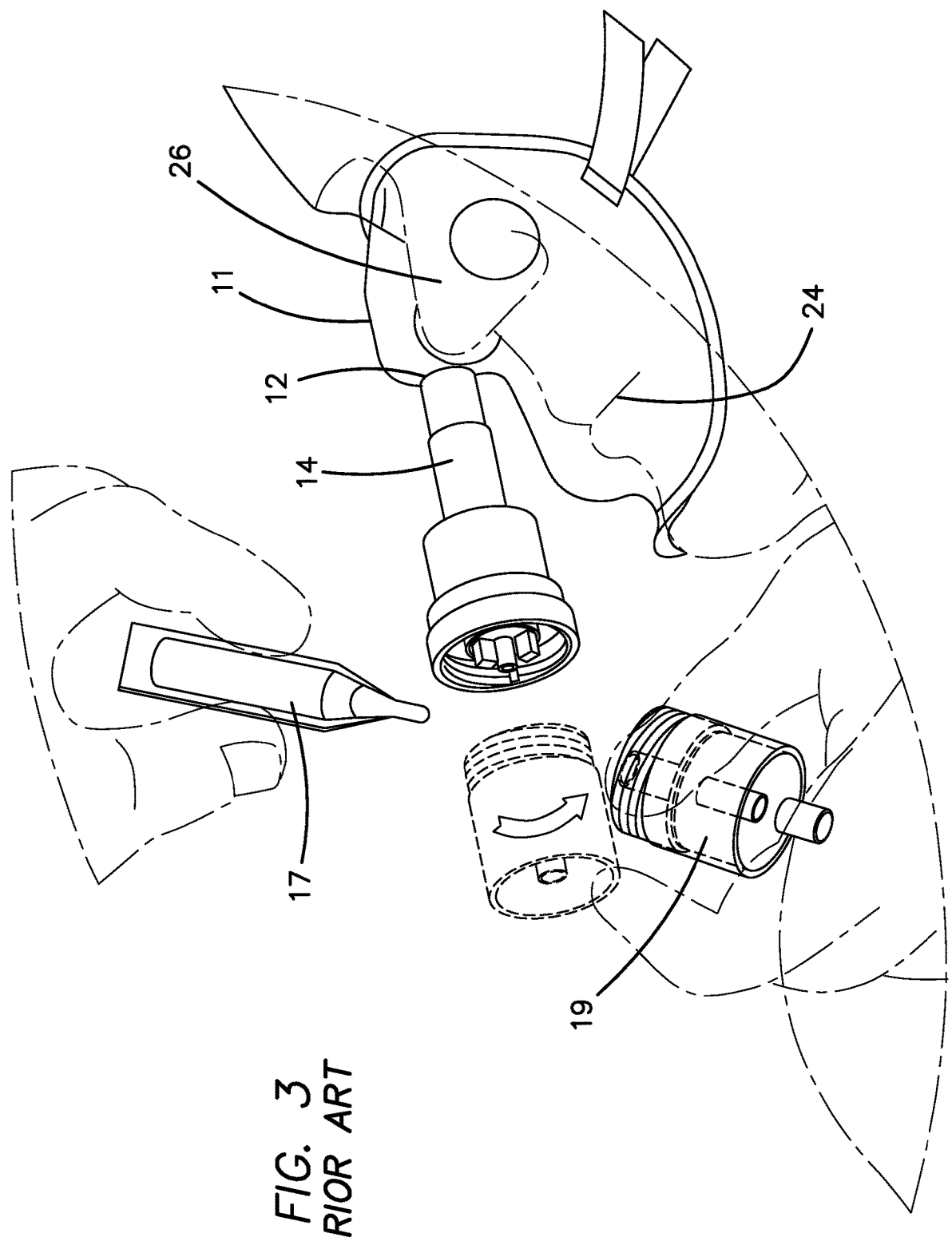
FIG. 3 is a magnified view of a prior art nebulizer apparatus being used for a patient lying on their back or at an angle.

In addition to the problems associated with disconnecting the medication reservoir from the nebulizer apparatus, a prior art nebulizer apparatus also fails to accommodate the variety of positions a patient may be treated in. This deficiency can become particularly problematic in the context of an emergency medical response. For instance, a prior art nebulizer apparatus requires that the medication reservoir of the apparatus be in a substantially upright position. FIGS. 2 and 3 illustrate the use of a prior art nebulizer apparatus 10 with a patient 20 lying on their back. The orientation of the patient prevents the medication reservoir 19 from being oriented vertically. The improper orientation of the medication reservoir 19 prevents the liquid medication within the medication reservoir 19 from being properly aerosolized and delivered to the patient 20, and the liquid medication may also spill into the face mask 11 of the apparatus 10, and, possibly, into the nose 26 and mouth 24 of the patient. Moreover, the addition of liquid medication using a syringe 17, or other suitable device, is difficult because the nebulizer apparatus must be disassembled to access the medication reservoir 19. In addition, the need to shut off the source of carrier gas is a further inconvenience.

Figure 4:
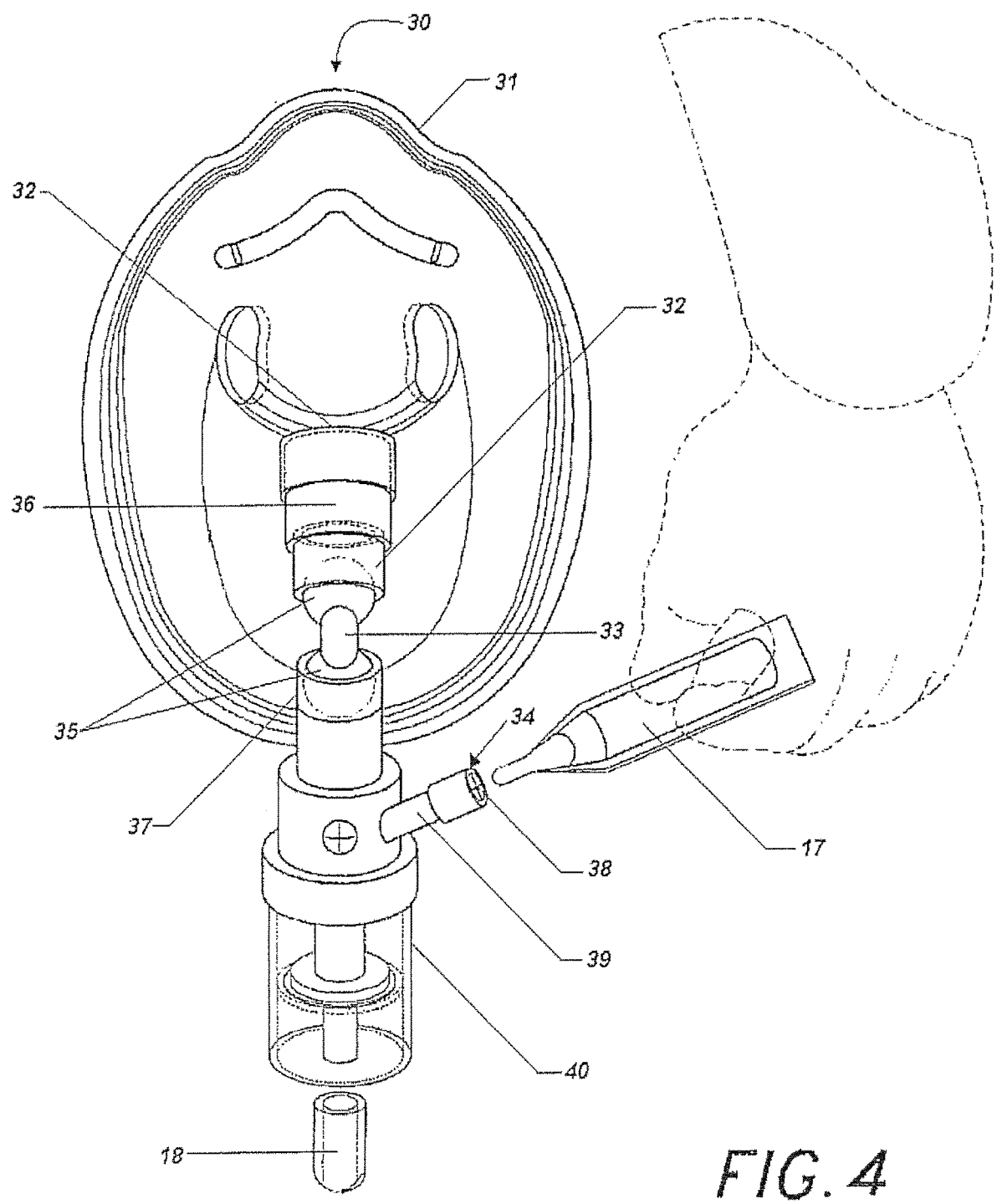
FIG. 4 is a front view of one embodiment of the nebulizer apparatus contemplated by the current invention, including: a face mask, a medication reservoir, a hollow ball and socket joint connecting the face mask to the medication reservoir, and a rapid injection port.

FIG. 4 illustrates a preferred embodiment of the inventive nebulizer apparatus. The nebulizer apparatus 30 includes a face mask 31 designed to enclose the nose and mouth of the patient. In a preferred embodiment, the face mask 31 is constructed of a flexible material, such as a flexible plastic, to fit comfortably on the face of the patient. The face mask may also include a compressible plastic bladder, or other pad, running along the edge of the portion of the mask that receives the patient's face, ensuring a snug and comfortable fit. In one preferred embodiment all of these components or at least those that contact the patient are designed for single use and are disposed of following that use.

The face mask 31 of the inventive nebulizer apparatus 30 is connected to a medication reservoir 40 through a housing 36, and a hollow member 33 having two, substantially spherical ends 35. The housing 36 is substantially tubular, with one end coupled to the face mask 31, and the other end 32 constructed to receive a spherical end of the hollow member 33. The spherical end of the hollow member 33 fits into the end 32 of the housing 36, resulting in a ball and socket connection between the housing 36 and the hollow member 33. Likewise, the other spherical end of the hollow member 33 fits into a receiving structure 37 of the medication reservoir 40, resulting in a ball and socket connection between the medication reservoir 40 and the hollow member 33.

The ball and socket connection between the hollow member 33 and both the housing 36 and the medication reservoir 40 allows a range of motion between the face mask 31 and the medication reservoir 40. In fact, the hollow member 33 may rotate with two degrees of freedom about its connection to either the housing 36 or the medication reservoir 40. As will be shown in FIGS. 5 and 6, the range of motion between the face mask 31 and medication reservoir 40 allows the nebulizer apparatus of the current invention 30 to effectively deliver aerosol medication to a patient in various positions, such as on their side, back, or stomach.

In an alternate embodiment of the current invention, the hollow member 33 may form a ball and socket connection directly with a receiving structure of the face mask 31. The direct connection of the hollow member 33 and the face mask 31 may simplify the manufacture of the inventive nebulizer apparatus, or improve its durability. In addition, the ball and socket connection between the hollow member 33 and the housing 36, face mask 31, or medication reservoir 40, may be disconnected, providing for easier storage and cleaning of the nebulizer apparatus 30 in situations where disposable apparatus is not used.

The medication reservoir 40, connected to the face mask 31 by the hollow member 33, is where liquid medication, such as albuterol, saline, or other medication, is intermixed with a carrier gas; such as oxygen or air, to create a medicated aerosol. The carrier gas is delivered to the inventive nebulizer apparatus 30 through tubing 18 connected to a gas source. The medicated aerosol flows from the medication reservoir 40 through the hollow member 33 and through the housing 36 to the face mask 31 of the nebulizer apparatus 30. Upon inhalation or exhalation of the patient, the medicated aerosol flowing to the face mask 31 is then delivered to the patient through their nose or mouth.

The liquid medication is introduced to the medication reservoir 40 through a rapid injection port 34. In one embodiment, the rapid injection port may be located on the side of the medication reservoir 40, and in a position towards the top of the medication reservoir 40, or in the receiving structure 37 of the ball and socket connection. It will be apparent that multiple injection ports can be supplied at different locations on the device—even on the ball and socket connector. Multiple injection ports permit additional doses of the initial medication or doses of a different medication to be in place for instantaneous injection when they are needed. The rapid injection port 34 includes a short inlet tube 39 extending outward from the outer surface of the medication reservoir 40. In the preferred embodiment, the short inlet tube 39 of the rapid injection port 34 is at a slight upward angle from the horizontal plane normal to the side wall of the medication reservoir 40.

One end of the short inlet tube 39 opens into the medication reservoir 40, with the other end terminating at a gate 38, composed, for example, of a flexible piece of plastic, fabric, or other material, for receiving a drug dispenser 17. In one embodiment, the gate 38 is composed a plurality of plastic sheets, defining a single plane, which fit snugly together along cuts radially placed from the center point of the gate. Upon placement of a dispenser 17 at the gate, the plurality of plastic sheets bend inward to receive the tip of the dispenser 17. Medication may then be delivered to the medication reservoir 40 through the gate 38 and through the short inlet tube 39.

The inventive nebulizer apparatus 30 may be fabricated from a flexible material such as plastic or rubber, or other materials. It may be desirable, however, for certain components, such as the housing 36, rapid injection port 34, hollow member 33, and medication reservoir 40, to be constructed of a strong, durable material, that need not be flexible, such as a stiff plastic, glass, or a polyester or epoxy resin. Moreover, it may be desirable that the materials comprising the face mask 31, housing 36, rapid injection port 34, hollow member 33, and medication reservoir 40 be transparent such that the medicated aerosol is visible in nebulizer apparatus 30.

Figure 5:
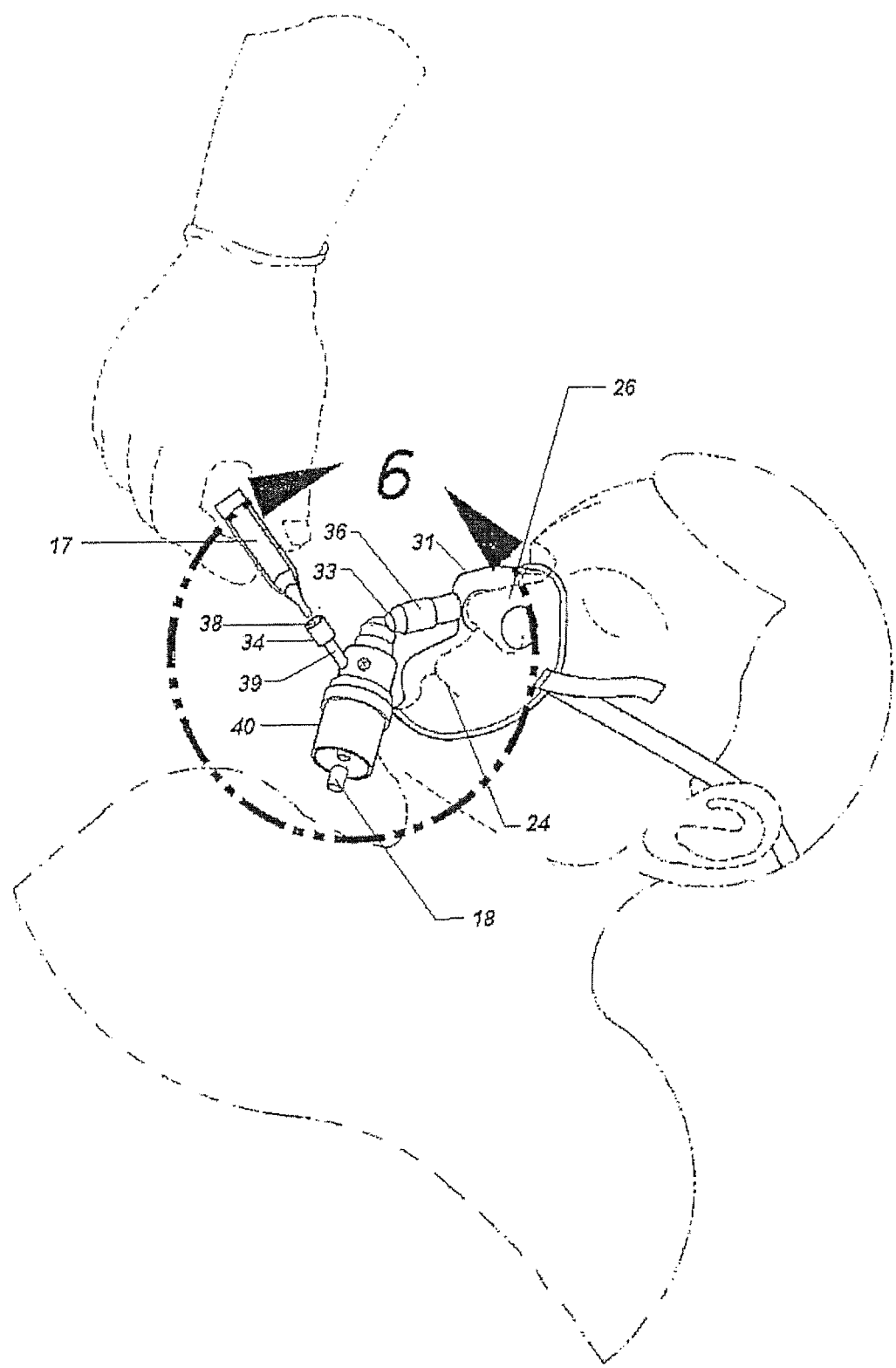
FIG. 5 is a side view of an embodiment of the nebulizer apparatus as contemplated by the current invention being used for a patient lying on their back or at an angle.
Figure 6:
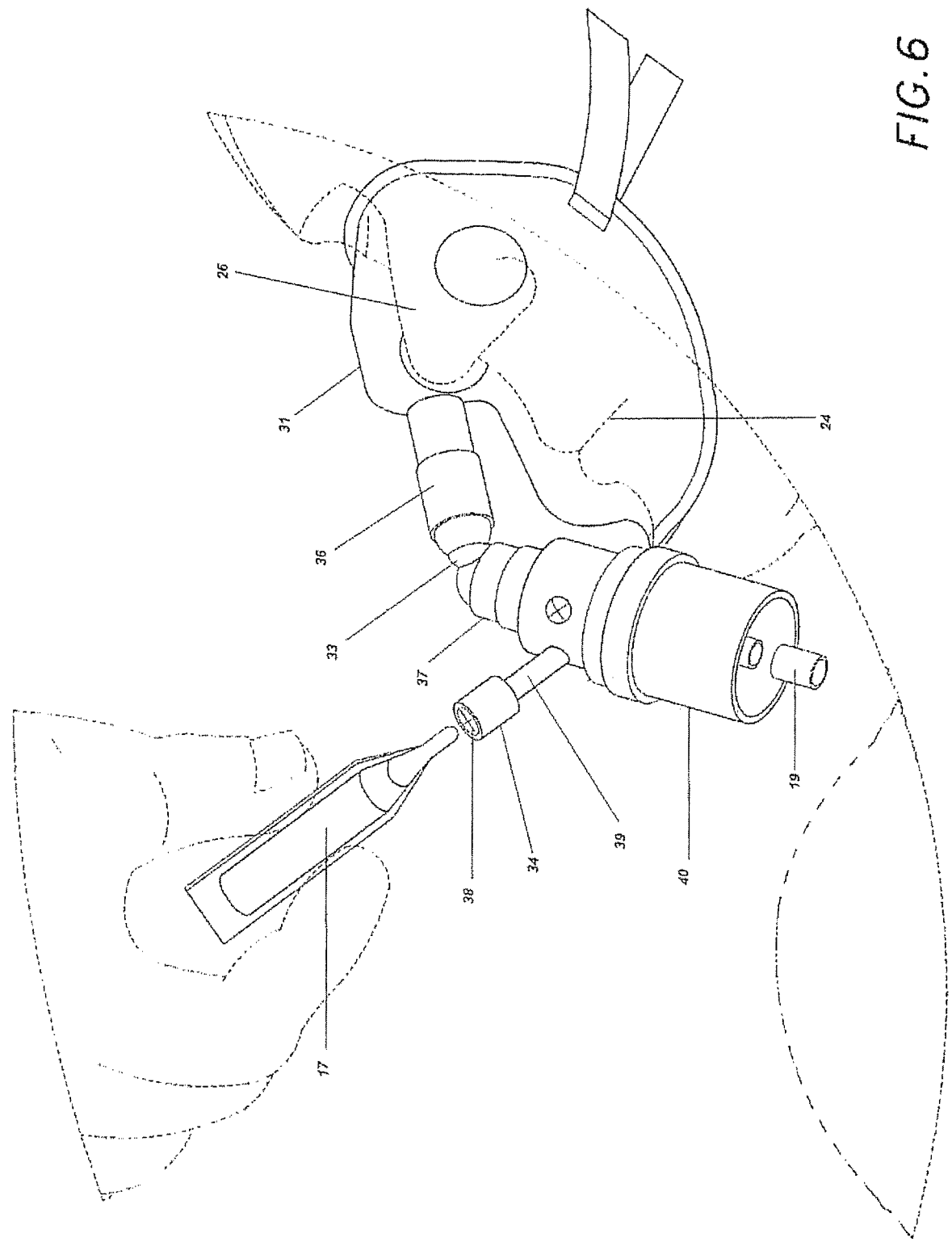
FIG. 6 is a magnified side view of one embodiment of the nebulizer apparatus as contemplated by the current invention being used for a patient lying on their back or at an angle.

The present invention provides an improved nebulizer apparatus with great advantages over the prior art. As shown in FIGS. 5 and 6, the ball and socket connections between the hollow member 33 and the housing 36, and medication reservoir 40 allow for the effective delivery of medicated aerosol to patients lying on their backs or in virtually any other position. The ball and socket connections ensure that the medication reservoir 40 is maintained in a substantially vertical orientation independent of the position of the patient. As a result, the liquid medication is properly aerosolized and delivered to the patient, and there is no spillage of the liquid medication.

Figure 7:
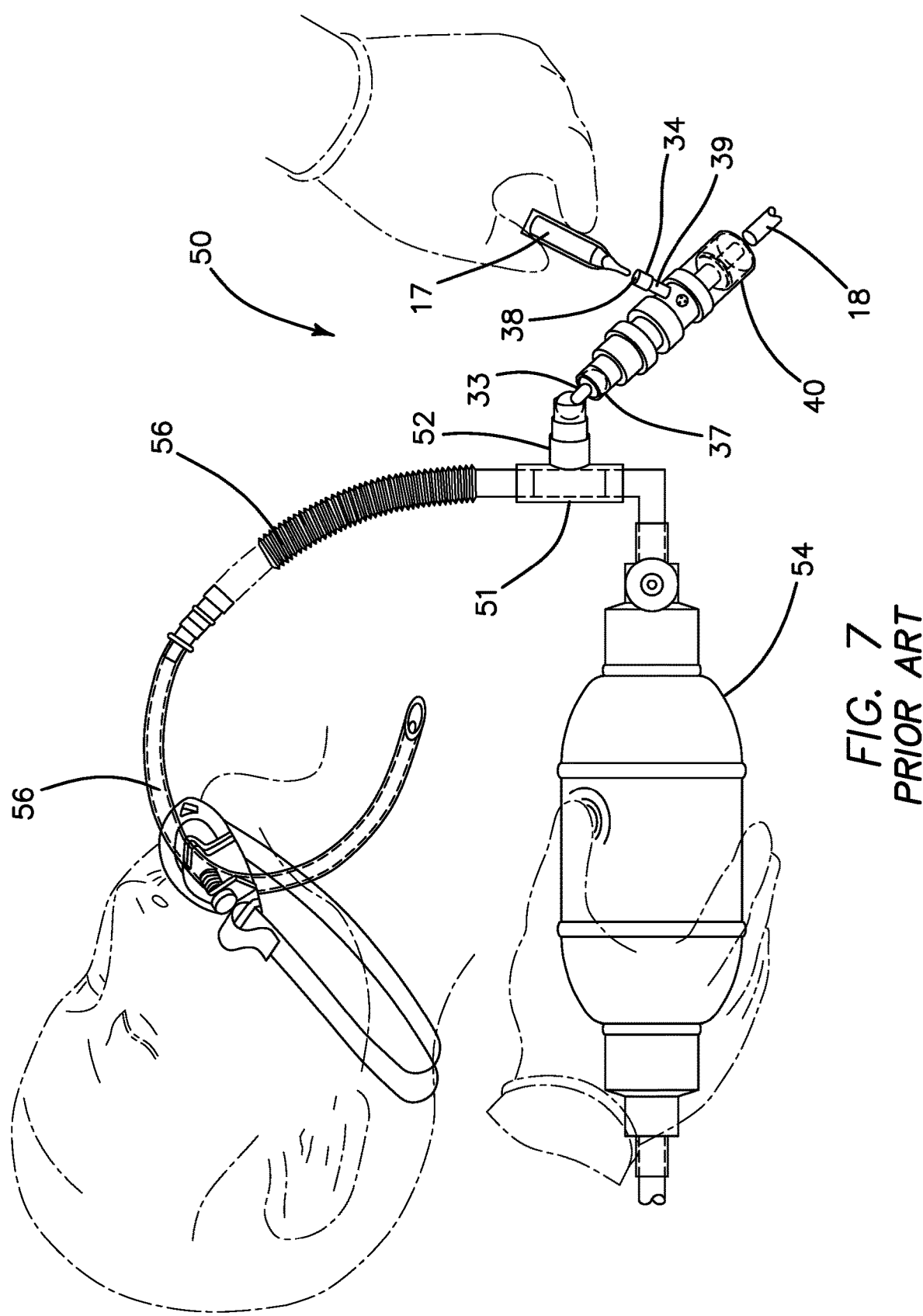
FIG. 7 is a side view of an alternate embodiment of the nebulizer apparatus of the current invention, including: a resuscitator bag, hosing, medication reservoir, hollow ball and socket joint, rapid injection port, and intubation tube.

An alternate embodiment of the nebulizer apparatus 50 for use with a resuscitator bag is depicted in FIG. 7. As in the previous embodiment the medication reservoir 40 contains a rapid injection port 34, and is connected to a conduit for carrier gas 18. A tubular member having two substantially spherical ends 33 couples to a receiving structure 37 on the top of the medication reservoir 40. The other spherical end of the tubular member 33 couples to a receiving structure 52 of a T-junction 51, or other tubular connector. The T-junction is further coupled to a resuscitator bag 54 and a flexible tube 58. The flexible tube may couple to a tube for intubation 56, such as an endotracheal tube, or a face mask.

Figure 8:
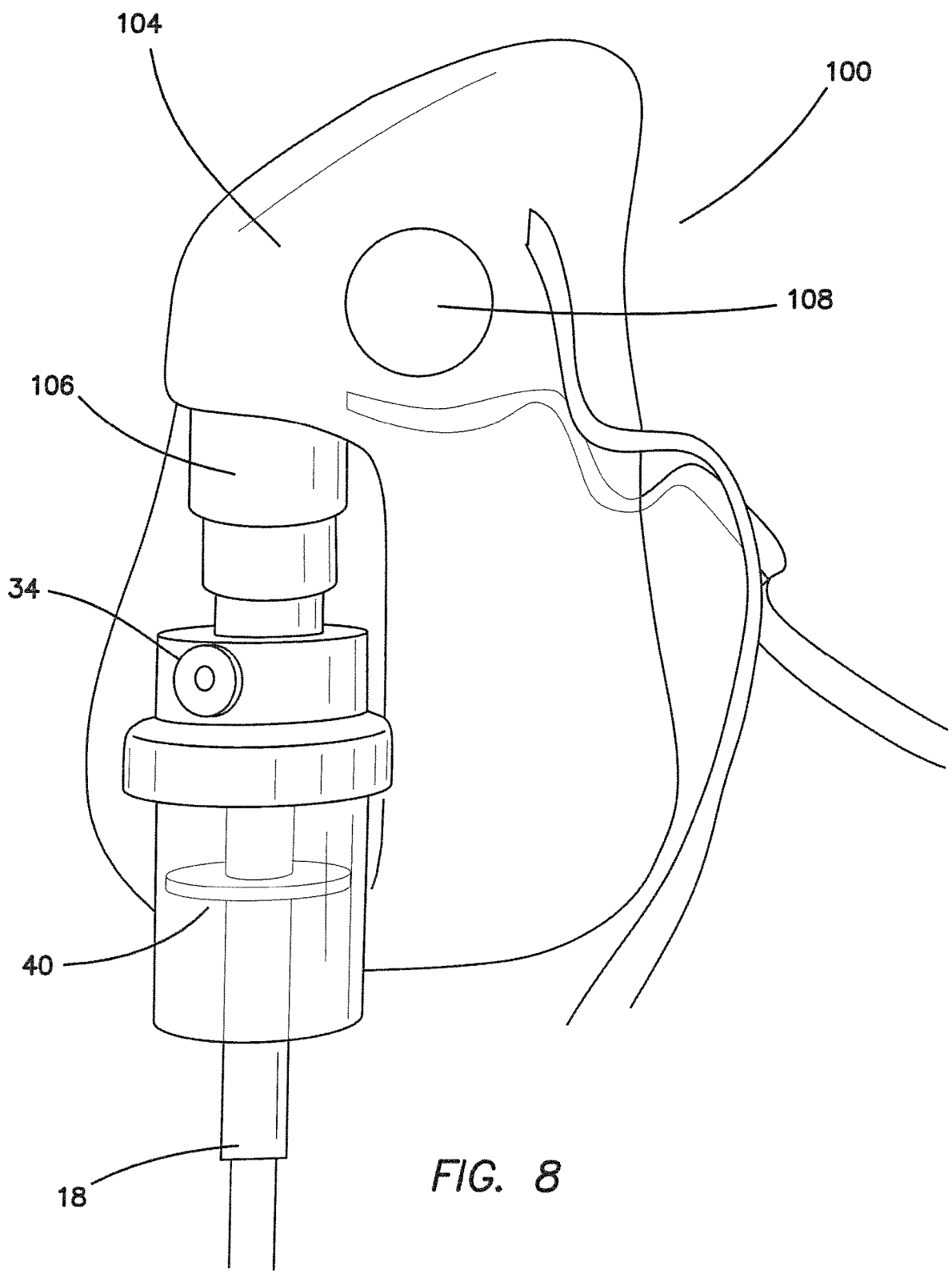
FIG. 8 is a side view of an alternate embodiment of the nebulizer apparatus of the current invention where the nebulizer is coupled directly to a face mask.
Figure 9:
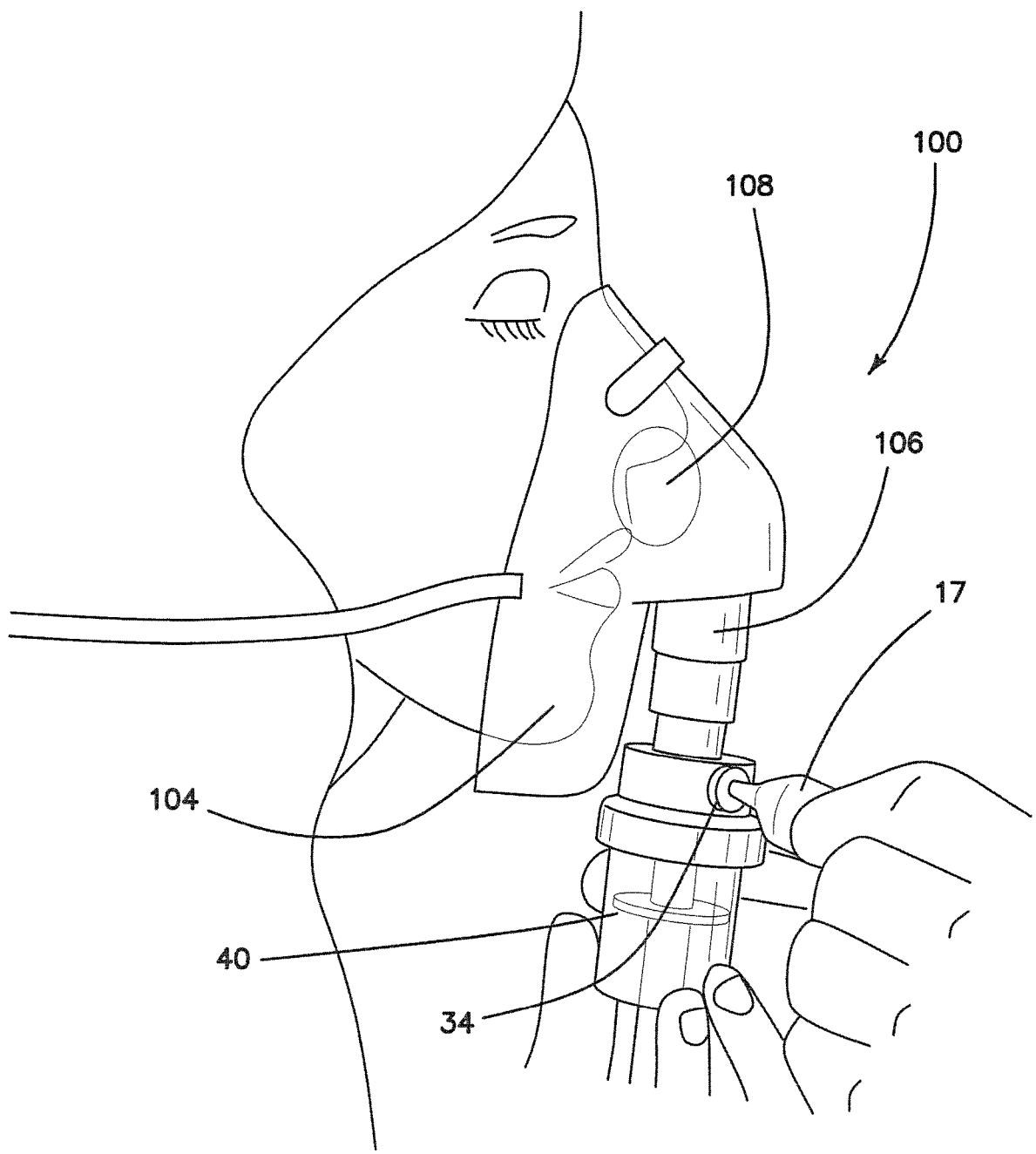
FIG. 9 is a side view of the alternate embodiment of the nebulizer apparatus seen in FIG. 8 when the face mask portion of the apparatus is applied to the face of a patient.

An alternative embodiment of the nebulizer apparatus 100 is seen in FIGS. 8 and 9. In this embodiment, the medication reservoir 40 comprises a rapid injection port 34 disposed directly in the reservoir 40 which may be accessed by the drug dispenser 17 as seen in FIG. 9. In other words, the rapid injection port 34 may be communicated directly with the internal volume of the medication reservoir 40 to allow direct deposit of the medication from the dispenser 17 thereby. The reservoir 40 is also directly coupled to a face mask 104 via a mask connector 106 disposed substantially beneath the nasal portion of the face mask 104. The face mask 104 also comprises a plurality of exhaust ports 108 also defined in the nasal portion of the face mask 104. To use the nebulizer apparatus 100, the face mask 104 is placed over the nose and mouth of a patient with the reservoir 40 already coupled to the mask connector 106 of the face mask 104. The medicated aerosol flows from the medication reservoir 40 through the hollow mask connector 106 and to the face mask 104 of the nebulizer apparatus 100. Upon inhalation or exhalation of the patient, the medicated aerosol flowing to the face mask 104 is then delivered to the patient through their nose or mouth. The exhalation of the patient is removed from the mask 104 by flowing through the exhaust ports 108. It should also be noted that the medication reservoir 40 may be coupled to the mask connector 106 via the ball and socket configuration described in detail above. The ball and socket connections between the mask connector 106 and medication reservoir 40 allow for the effective delivery of medicated aerosol to patients lying on their backs or in virtually any other position. The ball and socket connections ensure that the medication reservoir 40 is maintained in a substantially vertical orientation independent of the position of the patient. As a result, the liquid medication is properly aerosolized and delivered to the patient, and there is no spillage of the liquid medication.

Figure 10:
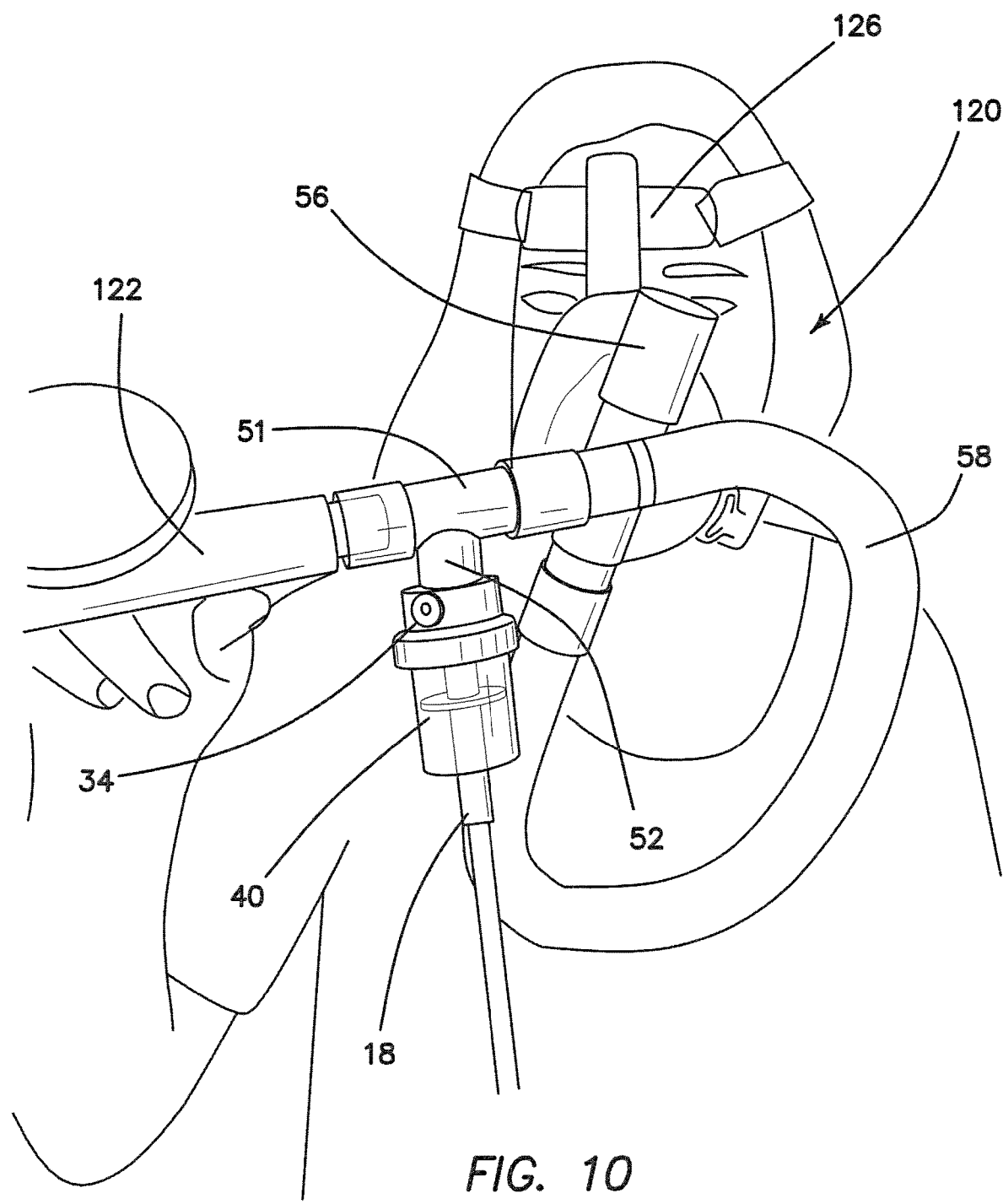
FIG. 10 is a perspective view of an alternate embodiment of the nebulizer apparatus of the current invention, including a first flexible tube coupled to a continuous positive airway pressure (CPAP) device, a second segment of flex tubing, hosing, medication reservoir, and T-junction.
Figure 11:
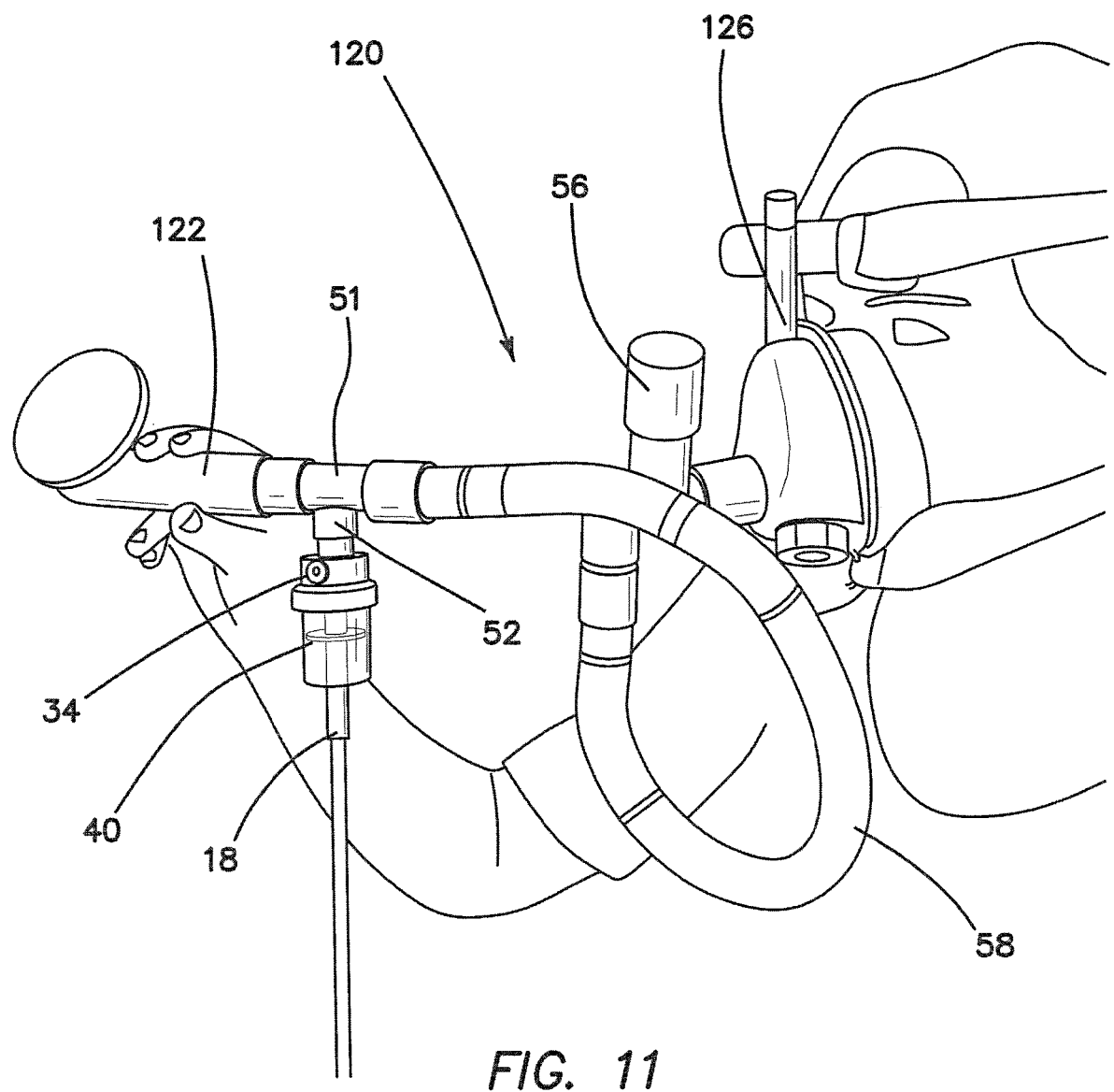
FIG. 11 is a side view of the alternate embodiment of the nebulizer apparatus seen in FIG. 10.

An alternate embodiment of the nebulizer apparatus 120 for use with a second segment of flex tubing 122 is depicted in FIGS. 10 and 11. As in the previous embodiment the medication reservoir 40 contains a rapid injection port 34 disposed directly into the reservoir 40 itself, and is connected to a conduit for carrier gas 18. Here, the reservoir 40 is coupled to a receiving structure 52 of a T-junction 51, or other tubular connector. The T-junction 51 is further coupled to a second segment of flex tubing 122 and a first flexible tube 58 also used in the previous embodiments noted above. The flexible tube 58 may be coupled to a tube for intubation 56, such as an endotracheal tube, or a continuous positive airway pressure (CPAP) device 126. It should also be noted that a resuscitator bag similar to what is seen in FIG. 7 may be coupled to the T-junction 51 at the same position and in place of the second segment of flex tubing 122. Finally, in a modified embodiment, the medication reservoir 40 may be coupled to the T-junction 51 via the ball and socket configuration described in detail above. The ball and socket connections between the T-junction 51 and medication reservoir 40 allow for the effective delivery of medicated aerosol to patients lying on their backs or in virtually any other position. The ball and socket connections ensure that the medication reservoir 40 is maintained in a substantially vertical orientation independent of the position of the patient. As a result, the liquid medication is properly aerosolized and delivered to the patient, and there is no spillage of the liquid medication.

Figure 12:
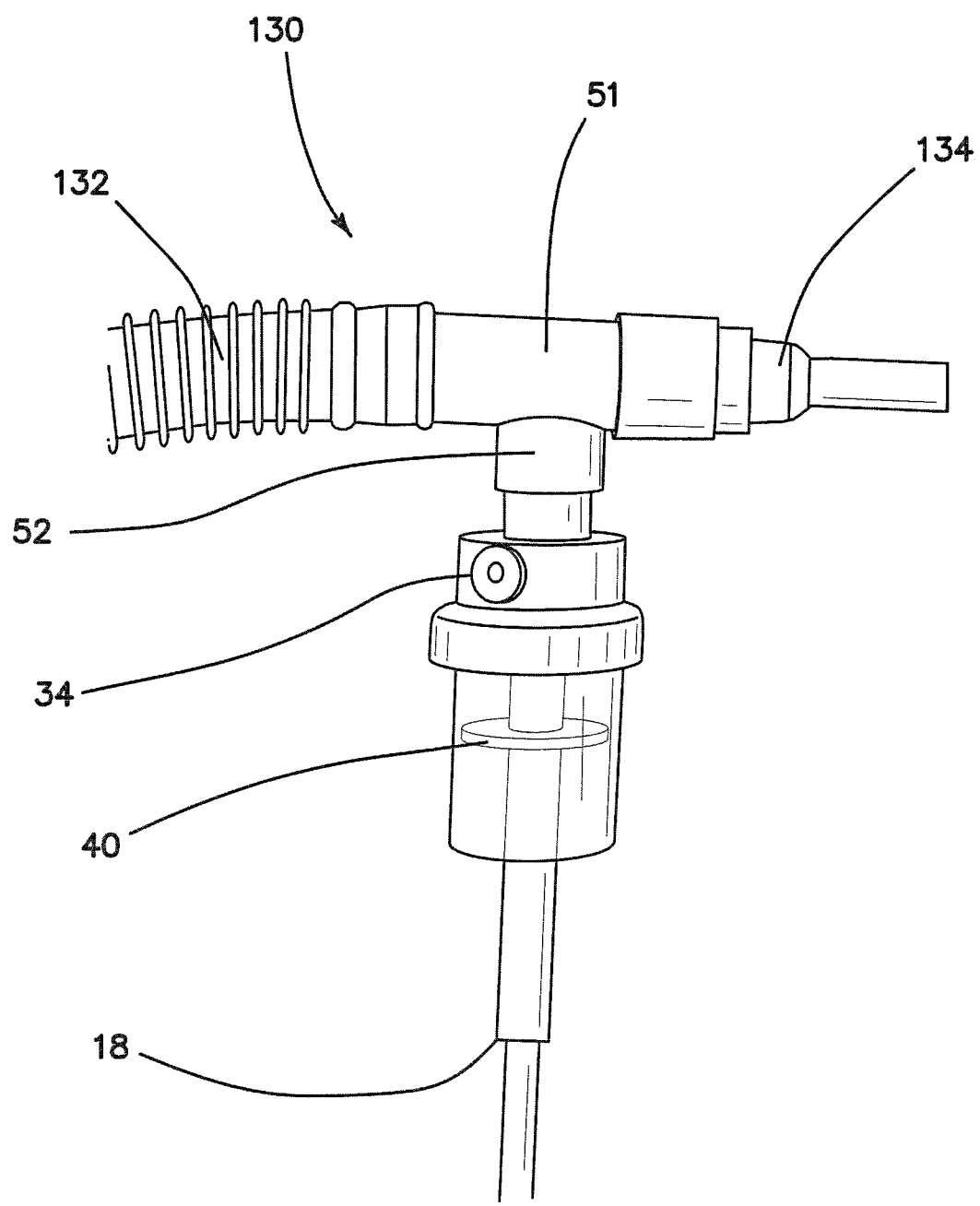
FIG. 12 is a side view of an alternate embodiment of the nebulizer apparatus of the current invention, including a flexible tube, mouthpiece, hosing, medication reservoir, and T-junction.
Figure 13:
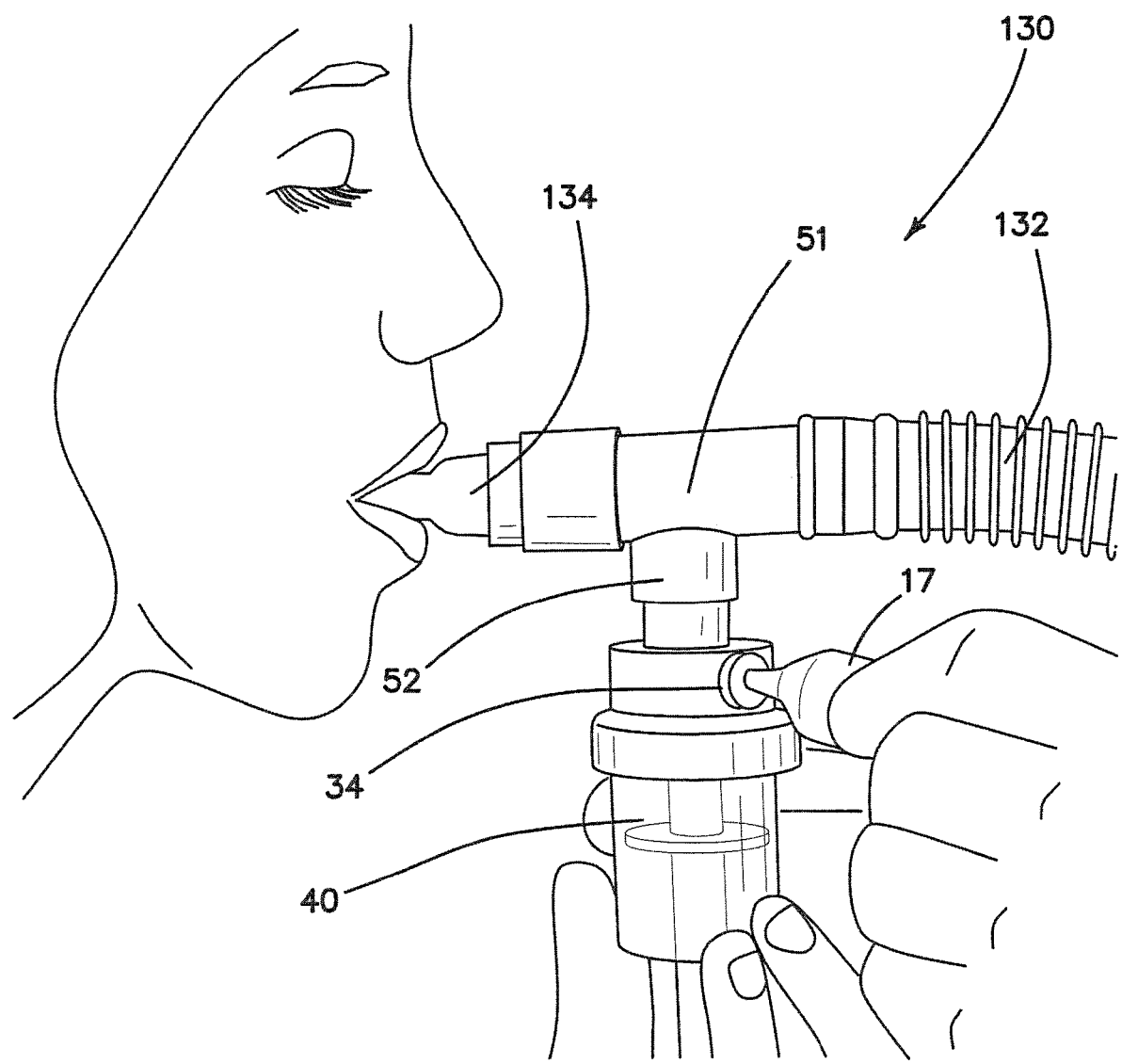
FIG. 13 is a side view of the alternate embodiment of the nebulizer apparatus seen in FIG. 12 when the mouthpiece portion of the apparatus is inserted into the mouth of a patient.
Figures 14, 15:
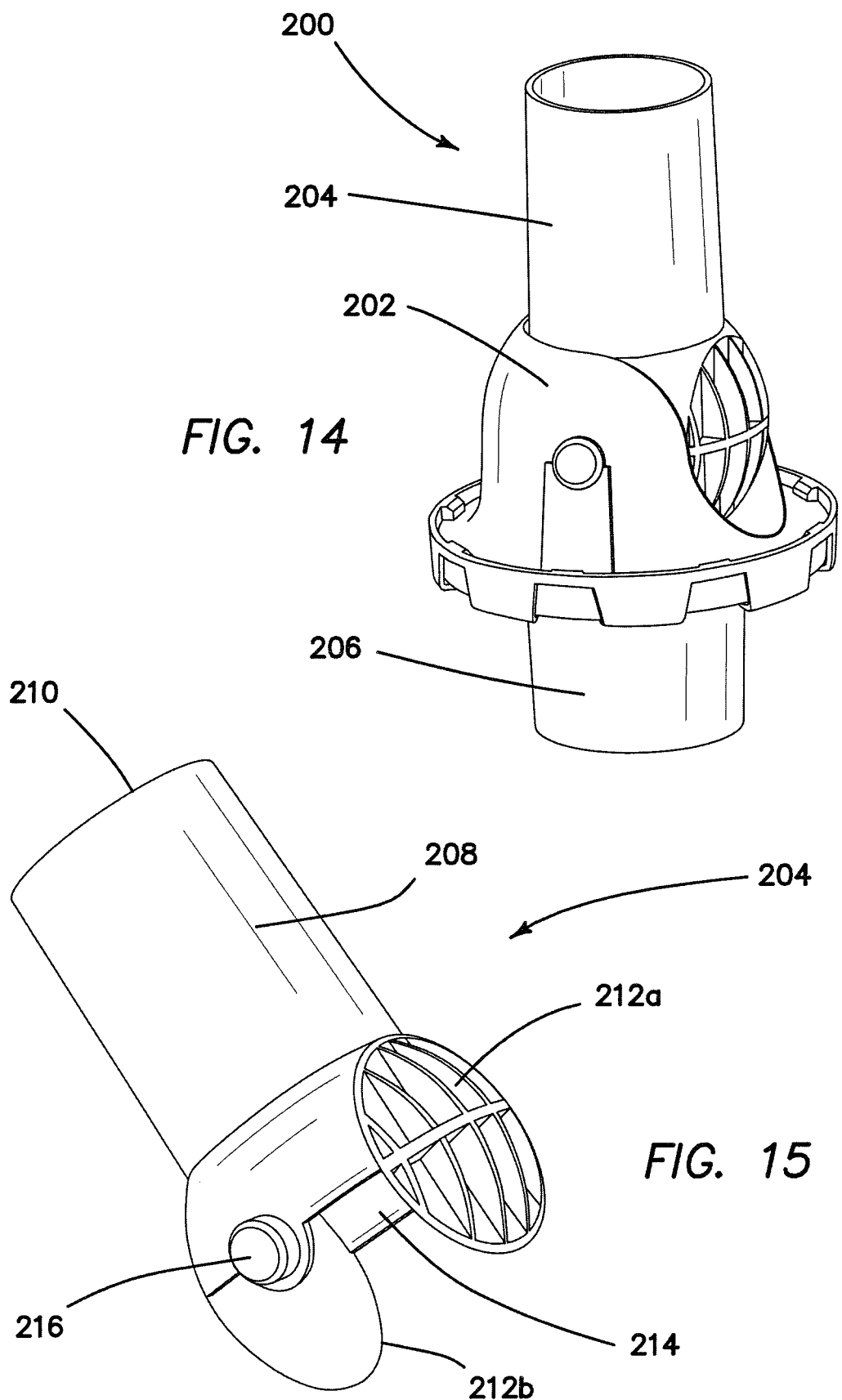
FIG. 14 is a perspective view of an alternate embodiment of the nebulizer apparatus comprising a swivel joint.
FIG. 15 is a magnified perspective view of the rotating airway portion of the nebulizer apparatus seen in FIG. 14.
Figure 16:
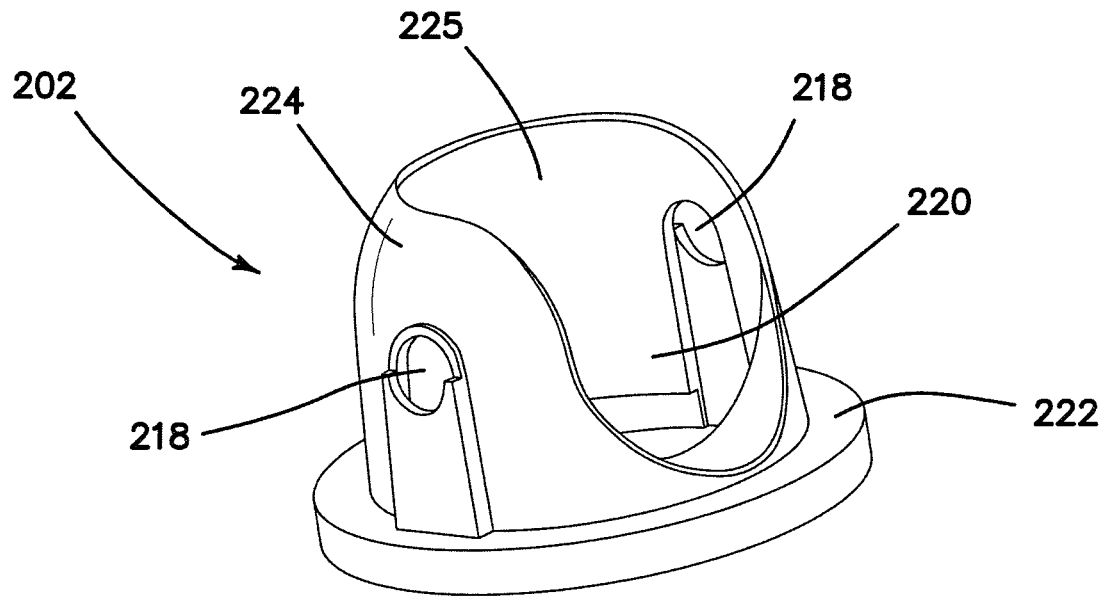
FIG. 16 is a magnified perspective view of the swivel housing portion of the nebulizer apparatus seen in FIG. 14.
Figure 17:
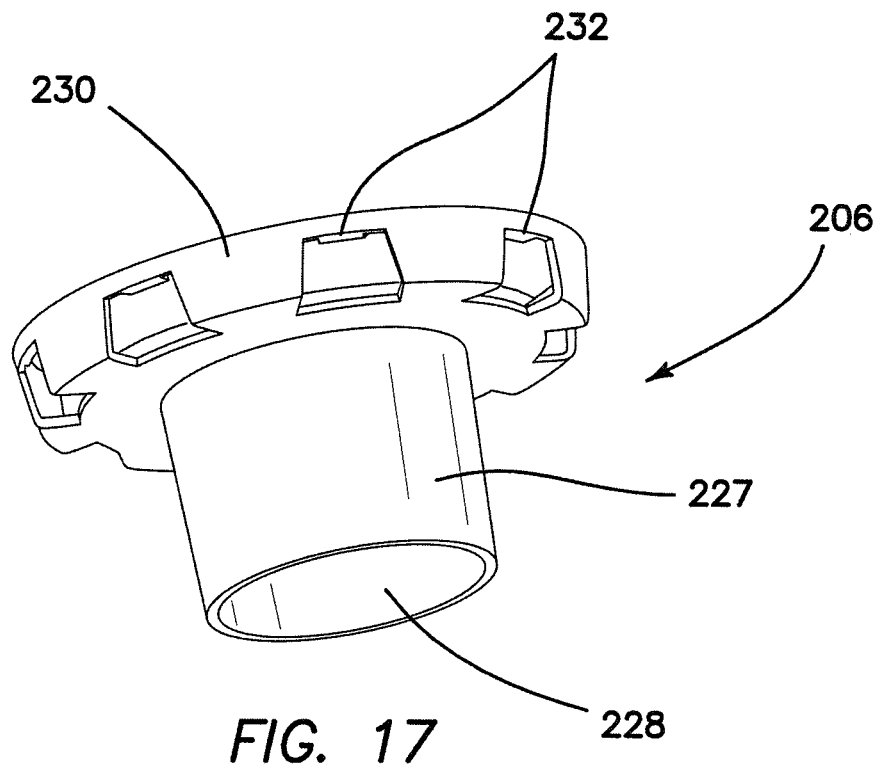
FIG. 17 is a magnified perspective view of the base coupling portion of the nebulizer apparatus seen in FIG. 14.
Figure 20:
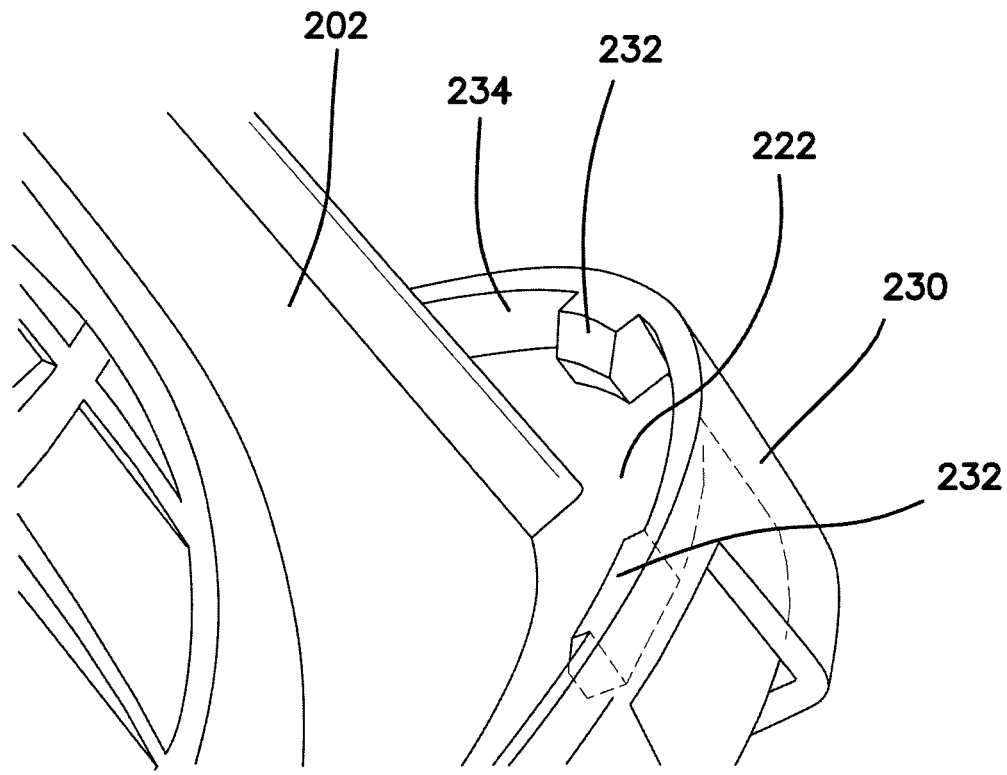
FIG. 20 is a magnified view of the coupling between the swivel housing and the base coupling portions of the nebulizer apparatus.
Figure 21:
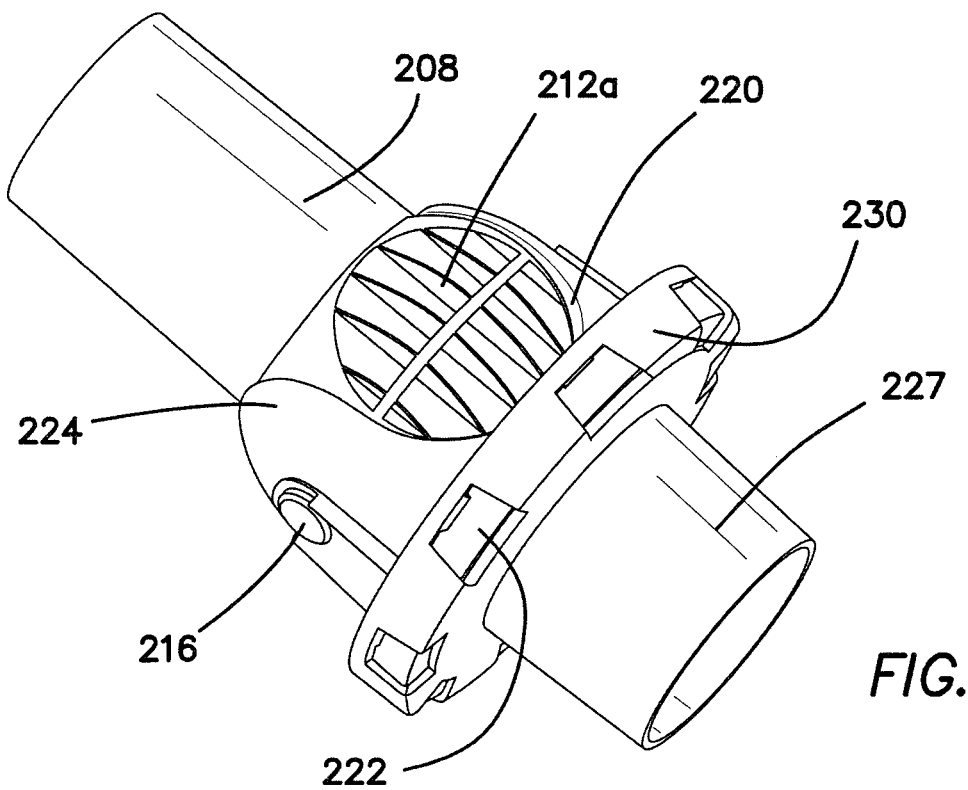
FIG. 21 is an alternative perspective view of the nebulizer apparatus seen in FIG. 14.
Figure 22:
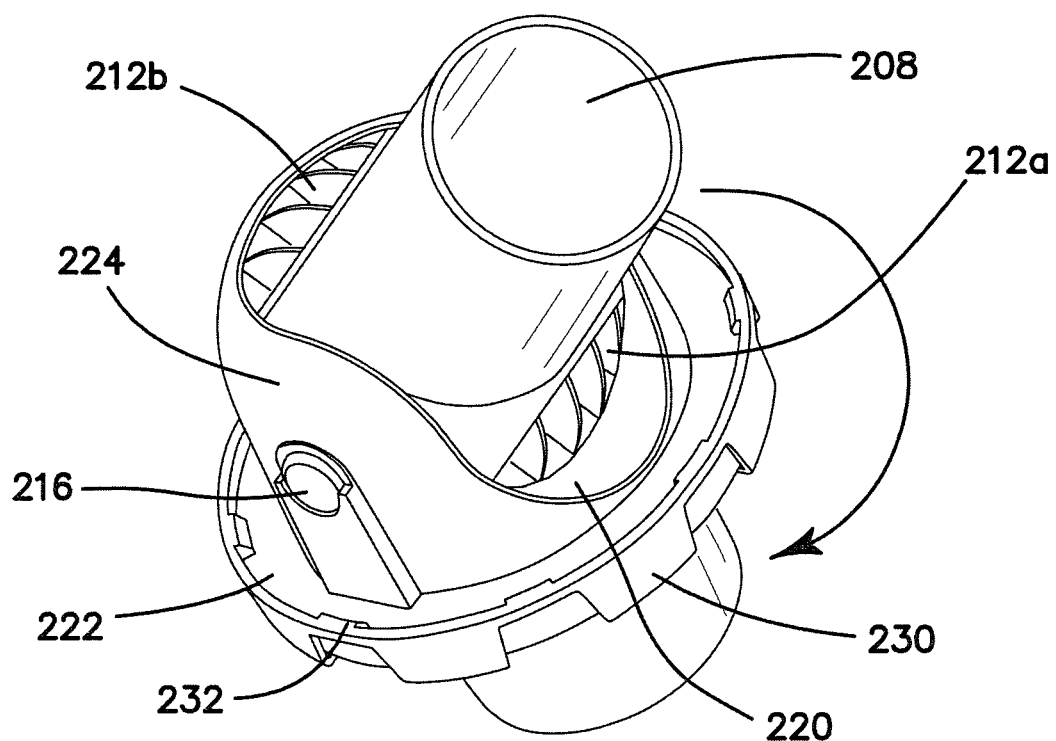
FIG. 22 is a perspective view of the nebulizer apparatus seen in FIG. 21 with the rotating airway portion orientated at an angle with respect to the base coupling portion.

Yet another embodiment of the nebulizer apparatus 130 is depicted in FIGS. 12 and 13. As in the previous embodiment the medication reservoir 40 contains a rapid injection port 34 disposed directly into the reservoir 40 itself, and is connected to a conduit for carrier gas 18. Here, the reservoir 40 is coupled to a receiving structure 52 of a T-junction 51, or other tubular connector. The T-junction 51 is further coupled to a segment of flex tubing 132 and a mouthpiece 134. The medicated aerosol flows from the medication reservoir 40 and is inhaled by the patient through the mouthpiece 134 as best seen in FIG. 13. The exhalation from the patient flows out of the distal end of the segment of flex tubing 132. It should also be noted that a resuscitator bag similar to what is seen in FIG. 7 may be coupled to the T-junction 51 at the same position and in place of the segment of flex tubing 132. Finally, in a modified embodiment, the medication reservoir 40 may be coupled to the T-junction 51 via the ball and socket configuration described in detail above. The ball and socket connections between the T-junction 51 and medication reservoir 40 allow for the effective delivery of medicated aerosol to patients lying on their backs or in virtually any other position. The ball and socket connections ensure that the medication reservoir 40 is maintained in a substantially vertical orientation independent of the position of the patient. As a result, the liquid medication is properly aerosolized and delivered to the patient, and there is no spillage of the liquid medication.

Another embodiment of the improved nebulizer apparatus comprising a swivel joint may be seen in FIGS. 14-23 and is generally denoted by reference numeral 200. The swivel joint 200 comprises a swivel housing 202 which accommodates a rotating airway 204. A removable base coupling 206 is further coupled to the bottom of the swivel housing 202. The swivel housing 202, rotating airway 204, and the base coupling 206 are all preferably comprised of low density polyethylene or polystyrene, however any plastic, plastic composite, or other material safe for use in human use may be used without departing from the original spirit and scope of the invention.

Detail of the rotating airway 204 and swivel housing 202 may be seen in FIGS. 15 and 16, respectively. The rotating airway 204 includes an airway tubing 208 with an opening 210 defined at its proximal end and a pair of cored out ears 212 onto which substantially arc shaped reinforcing ribs 212A and 212B are integrally formed on the exterior surface at the distal end of airway 204. The pair of ribs 212A, 212B are curved segments of a spherical surface so that the exterior rounded surface of each rib 212A, 212B faces away from the center longitudinal line of the airway tubing 208 as best seen in FIG. 15. The ribs 212A, 212B are also disposed or otherwise joined to the airway tubing 208 via an apex or a top most portion of each of the ribs 212.

The swivel housing 202 seen in FIG. 16 includes a body 224 which in turn includes an airway opening 220 into which airway 204 will rotate and a pair of pivot holes 218 defined in its surface. Disposed circumferentially around a bottom portion of the body 224 is a substantially circular base 222. The swivel housing 202 further defines an internal cavity 225 with circular opening 226 defined through base 222 and into body 224 as best seen in FIGS. 18 and 19. The airway opening 220 in the side of body 224 is substantially U-shaped and is defined in both a top portion and a side wall of the body 224 to allow airway 204 when pivoting about the axis defined through pivot holes 18 is allowed to move from a vertical in-line orientation shown in FIG. 14 to a perpendicular or radial extending orientation in FIG. 23. When the rotating airway 204 is disposed within the swivel housing 202 as seen in FIG. 19, one of the cored out ears 212, namely that one on which ribs 212A are provided as seen in FIG. 19, is accommodated or disposed within the opening 220 defined in body 224 with its curvature matching the curvature of the opening defined in body 224 so that a substantially airtight seal between the rotating airway 204 and swivel housing 202 is created in this position.

Returning to FIG. 15, the rotating airway 204 further includes a lower skirt 214 integrally formed with and extending between the pair of cored out ears 212, the center of the skirt 214 is aligned with the longitudinal center of the pair of cored out ears 212. Disposed on either side of the skirt 214 and between the ears 212 is a pivot pin 216. When the rotating airway 204 is disposed within the swivel housing 202 as seen in FIG. 19, each of the pivot pins 216 is accommodated or disposed into one of the corresponding pair of pivot holes 218 so that the rotating airway 204 is able to rotate about pivot pins 216 as is further described below.

Greater detail of the base coupling 206 may be seen in FIG. 17. The base coupling 206 comprises base tubing 227 with an inlet 228 defined at its distal end and a coupling portion 230 at its proximal end. The coupling portion 230 is substantially circular in shape and is disposed around the circumference of the base tubing 227. The coupling portion 230 also comprises a plurality of snaps 232 disposed symmetrically around the circumference of an inner lip 234 disposed on the inner surface of the coupling portion 230 as best seen in FIG. 20, which snaps 232 resilient snap fit onto base 222.

The swivel joint 200 is assembled by first inserting the airway tubing 208 of the rotating airway 204 into the opening 226 of the swivel housing 202 in the direction shown by the arrow seen in FIG. 18 as indicated by the arrow. The airway tubing 208 enters the internal cavity 225 of the swivel housing's body 224 and then exits the body 224 through an upper portion of the airway opening 220 as the rotating airway 204 is pushed through the swivel housing 202. As the rotating airway 204 moves through the swivel housing 202, the pivot pins 216 move against the inner surface of the internal cavity 225 until reaching the position of pivot holes 218, at which point each the pivot pins 216 enter each of the corresponding pivot holes 218, thus preventing further vertical displacement of the rotating airway 204 with respect to the swivel housing 202. Placement of the pivots 216 within the pivot holes 218 also ensures that ribs 212A, 212B of the rotating airway 204 are correctly centered and in place within the airway opening 220 as seen in FIG. 19. FIG. 19 explicitly shows rib 212A being positioned within the airway opening 220, however the opposing ribs 212B could also be chosen to be disposed within the airway opening 220 without departing from the original spirit and scope of the invention or altering the performance of the swivel joint 200 in any way. The base coupling 206 is then coupled to the swivel housing 202 by pressing the coupling portion 230 against the base 222 in the direction shown by the arrow depicted in FIG. 19. The base 222 is specifically pressed against the angled surfaces of the snaps 232 until the base 222 fits under the snaps 232 as best seen in FIG. 20. After the base coupling 206 has been joined to the swivel housing 202, a completed swivel joint 200 is formed as seen in FIG. 21.

When the base 222 has been fully inserted under all of the plurality of snaps 232, the swivel housing 202 is prevented from moving vertically with respect to the base coupling 227, however because the snaps 232 are disposed only at the top most portion of the inner lip 234 with a predetermined small clearance or tolerance, the swivel housing 202 is still free to rotate with respect to the coupling portion 230 of the base coupling 206. For example, the swivel housing 202 is free to rotate in the clockwise direction with respect to the base coupling 206 as indicated by the direction denoted by the arrow seen in FIG. 22. Counterclockwise rotation is equally possible. Additionally as seen in FIG. 22, the rotating airway 204 may be rotated within the airway opening 220. Specifically, the rotating airway 204 rotates about the pivot pins 216 disposed within the pivot holes 218 defined on either side of the body 224 of the swivel housing 202. As the rotating airway 204 is rotated downwards towards the base 222, the forward facing ribs 212A are rotated past the upper edge of the airway opening 220 while at the same time ribs 212B are further exposed at the opposing end of the airway opening 220. The ribs 212A, 212B thus cooperate to ensure that at no point, regardless of the orientation of the rotating airway 204, is the internal cavity 225 freely exposed to the ambient environment other than through the restricted pathways defined by the ribs 212A and 212B. Thus, some leakage may be tolerated, particularly since the applied pressures are low. It is also within the scope of the invention that reinforcing ribs 212A and 212B could be defined on the inner surface of cored out ears 212 with the exterior surface of cored out ears 212 forming smooth spherical segments along with the adjacent upper surfaces of skirt 214, which will effectively seal with the adjacent circular edges of body 224 with which they are in contact.

Figure 23:
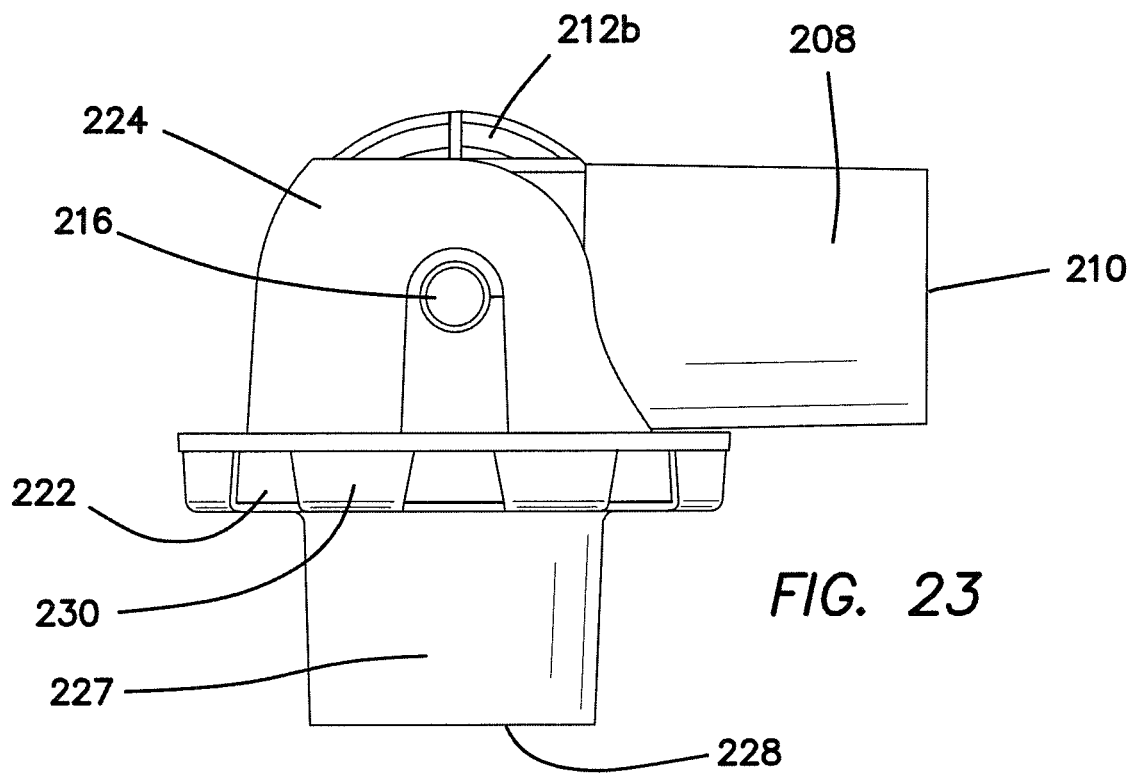
FIG. 23 is a side view of the nebulizer apparatus seen in FIG. 21 with the rotating airway portion orientated at a perpendicular orientation with respect to the base coupling portion.

The swivel joint 200 may be seen in the fully pivoted position in FIG. 23 with the rotating airway 204 moved down into a fully horizontal position, thus creating a 90 degree bend with respect to the base tubing 227 portion of the base coupling 206. The inlet 228 of the base tubing is further be coupled to a reservoir 40 seen in FIGS. 8-13. Additionally, a mouthpiece such as that seen in FIG. 13 may be coupled to the opening 210 of the airway tubing 208, or alternatively, a patient may insert the proximal end of the airway tubing 208 directly into their mouth. Medication from the reservoir 40 enters the base tubing 227 of the base coupling 203 and from there enters the internal cavity 225 the body 224 of the swivel housing 202. The direction of medication flow then follows the airway tubing 208 which has been rotated about the pivots 216 to the appropriate orientation as determined by the user/patient where the medication is then delivered to and inhaled by the patient. By simultaneously or sequentially rotating the swivel housing 202/rotating airway 204 with regard to the base coupling 206, and manipulating the orientation of the rotating airway 204 with regard to the swivel housing 202 in either or both of two mutually orthogonal axes of rotation, a user may orientate the swivel joint 200 in nearly any direction allowing the patient to receive nebulization in nearly any setting including when the patient is laying, sitting, or transitioning between positions. Precise orthogonality of the axes is not required. It is only preferred that the two axes are at least partially orthogonal or have a component of their axial direction orthogonal to the other axis.

Figure 24:
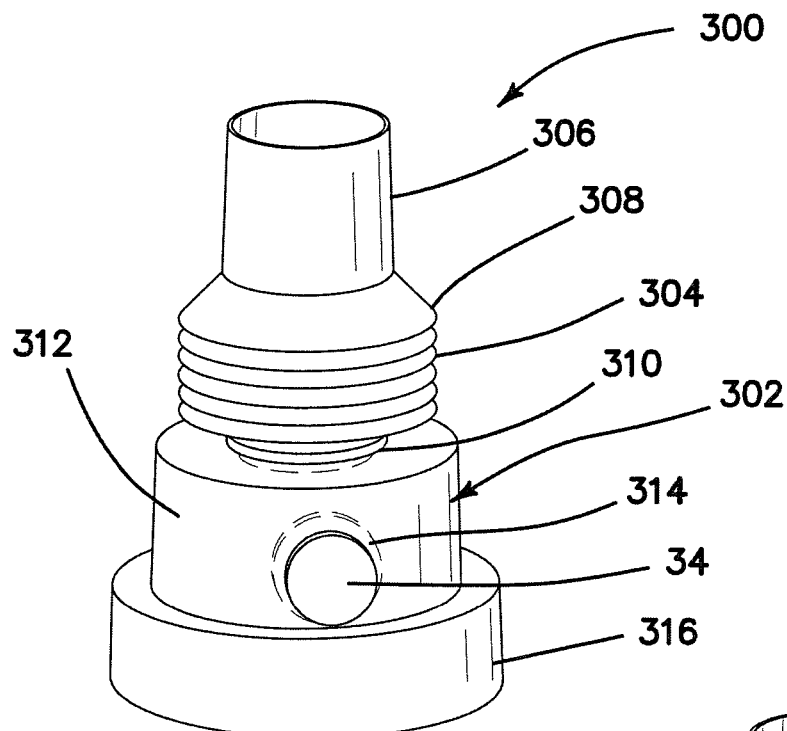
FIG. 24 is a perspective view of an alternate embodiment of the nebulizer apparatus comprising a collapsible joint.
Figure 25:
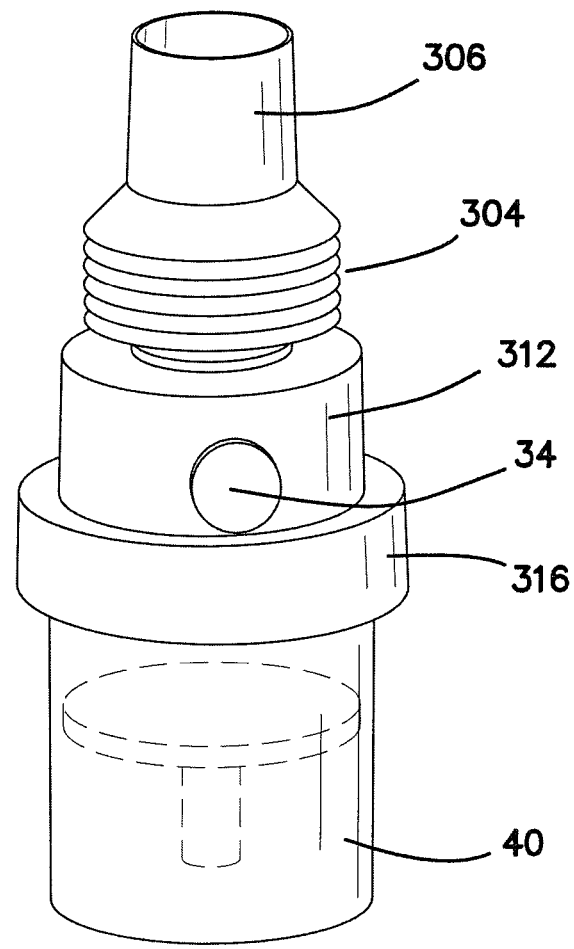
FIG. 25 is a perspective view of the nebulizer apparatus seen in FIG. 24 coupled to a medication reservoir.

Still another embodiment is shown in FIG. 24 as a collapsible joint, generally denoted by reference numeral 300. Collapsible joint 300 includes a housing 302 which accommodates a collapsible airway 304. Airway 304 is formed with a wall in the form of a bellows comprised of multiple frustoconical sections and is composed of flexible plastic so that airway 304 can be flexed in any direction and longitudinally extended or compressed along its longitudinal axis as shown best in FIGS. 27 and 28. The top of airway 304 is connected to a cylindrical extension or nipple 306 preferably comprised of a rigid plastic. The bottom of airway 304 is connected to similar rigid cylindrical extension 310 integrally formed with housing 302 and extending longitudinally therefrom. Housing 302 in the illustrated embodiment is cylindrical and extends from extension 310 into a cylindrical bell cap 312 into which a radial bore 314 is defined. A soft elastomeric rapid injection port 34 is then disposed into bore 314. Below bell cap 312 housing 302 integrally expands into a collar 316 into which reservoir 40 is coupled as described above as best shown in FIG. 25. Reservoir 40 may be compression fit into collar 316 or collar 316 may be provided with internal threading (not shown) into which external threading (not shown) of reservoir 40 is engaged.

Figure 26:
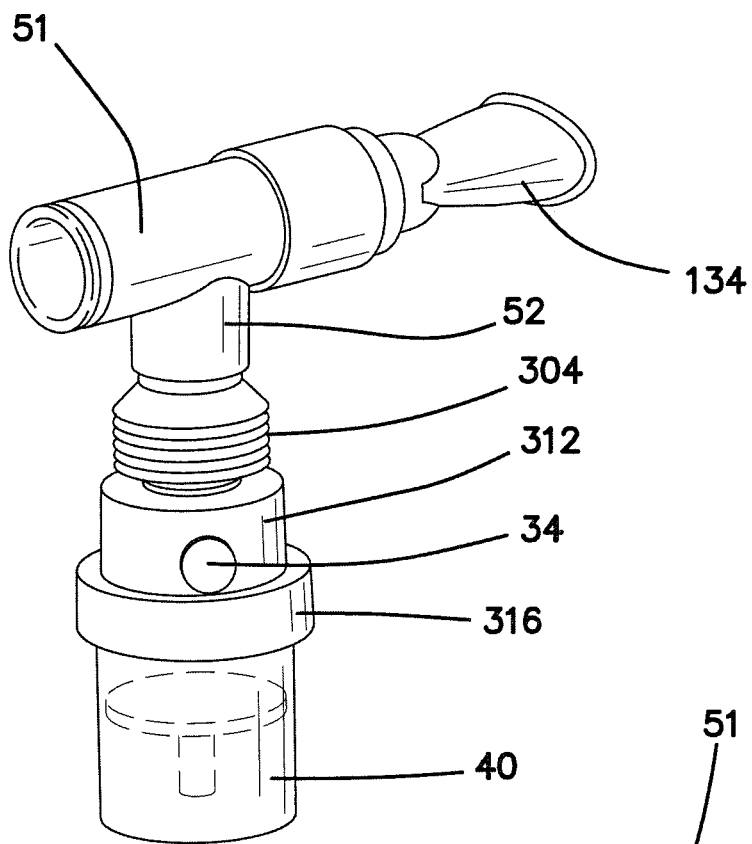
FIG. 26 is a perspective view of the nebulizer apparatus seen in FIG. 24 coupled to a receiving portion and mouthpiece.
Figure 27:
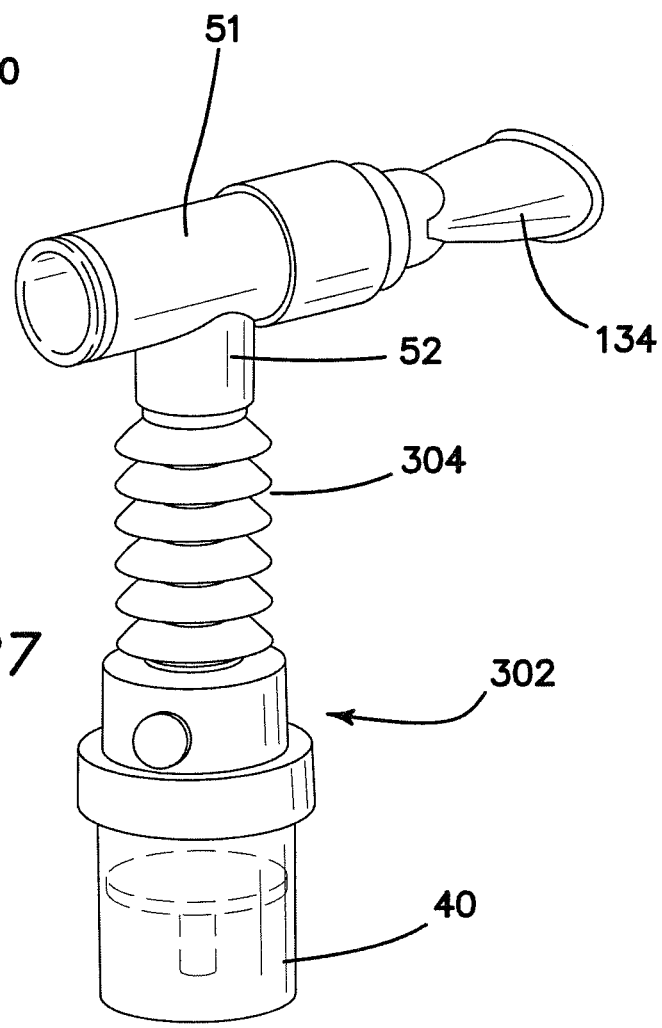
FIG. 27 is a perspective view of the nebulizer apparatus seen in FIG. 26 with the collapsible joint in the extended configuration.
Figure 28:
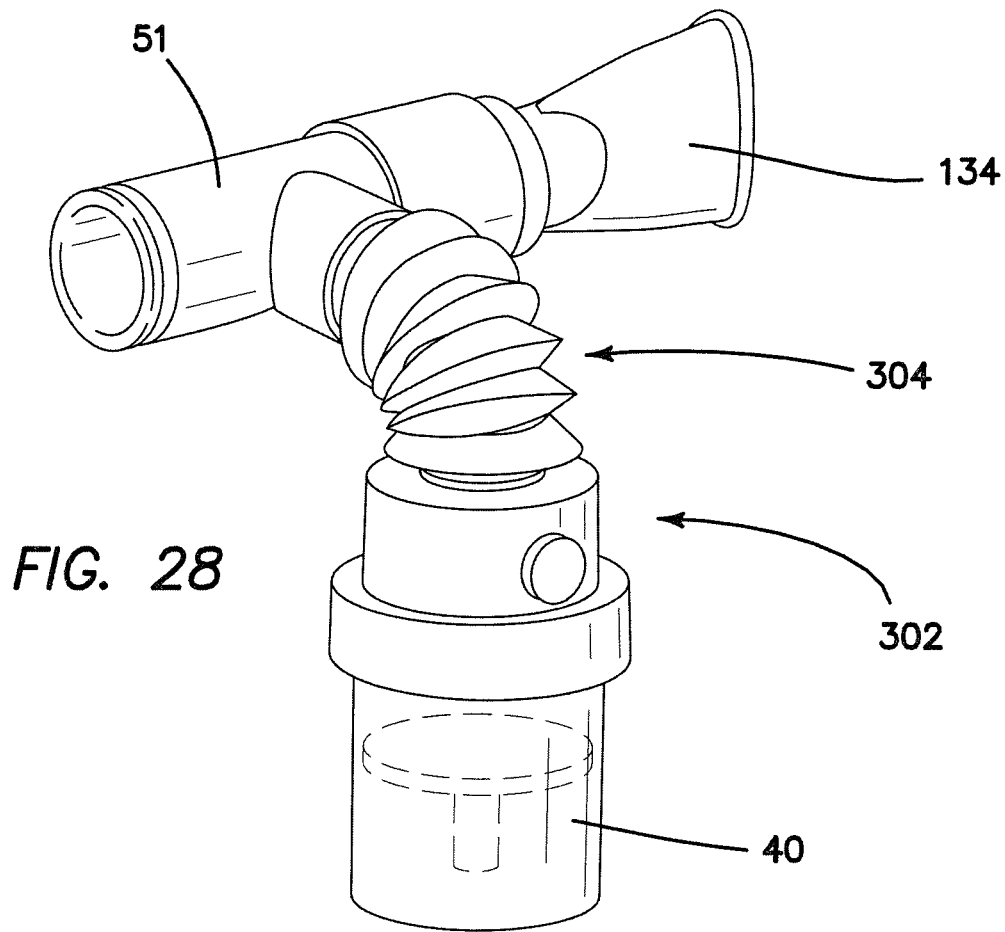
FIG. 28 is a perspective view of the nebulizer apparatus seen in FIG. 26 with the collapsible joint in the extended configuration and the mouthpiece orientated at an angle with respect to the medication reservoir.

Any one of the receiving structures or applicators illustrated in the embodiments above may then be coupled to extension 306. For example, the mouthpiece 134 of FIG. 13 may be compression fit onto Tee junction 51, which in turn is compression fit onto extension 306 by means of receiving structure 52 as shown in FIG. 26. Collapsible airway 304 is then able to accordion out as depicted in FIG. 27 allowing the vertical separation between mouthpiece 134 and reservoir 40 to be adjusted to a range of distances. The bellows construction allows airway 304 to be lengthened without any substantial tendency to resiliently reassume its original length. Additionally, airway 304 can be bent in any direction at any condition of longitudinal extension to provide a selected relative angular orientation that may be desired between mouthpiece 134 and reservoir 40 as shown in FIG. 28 without any substantial tendency of airway 304 to resilient return to its original angular configuration.

Figure 29:
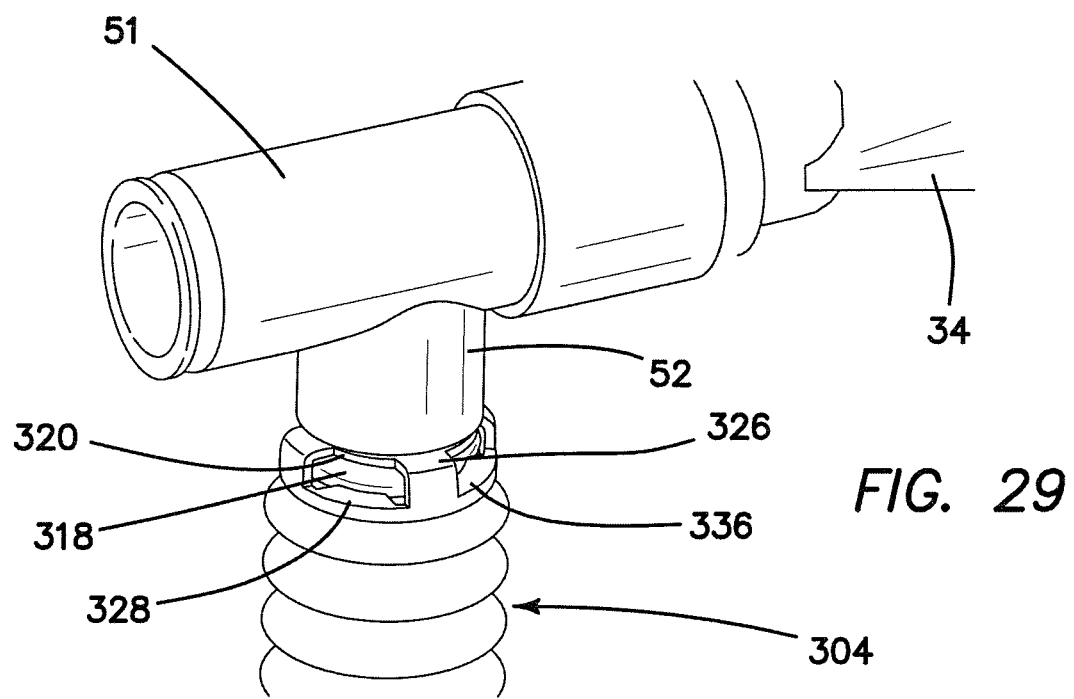
FIG. 29 is a magnified view of the coupling between the collapsible joint and the mouthpiece.
Figure 30:
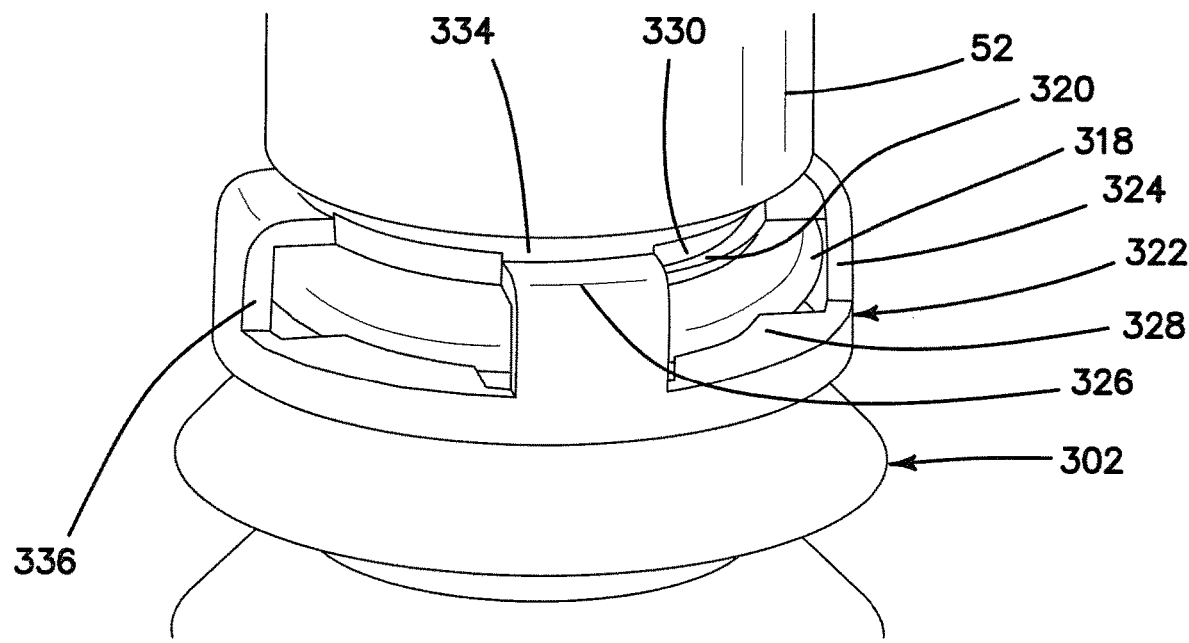
FIG. 30 is a magnified view of the coupling between the collapsible joint and the mouthpiece seen in FIG. 29.
Figure 31:
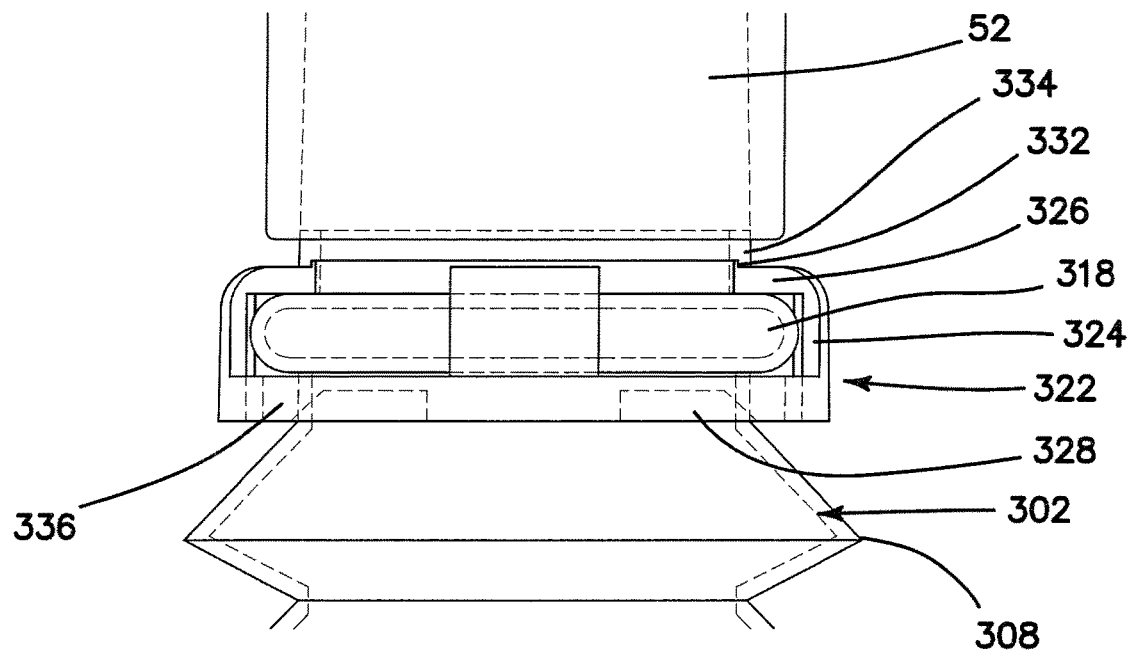
FIG. 31 is a cross section view of the coupling between the collapsible joint and the mouthpiece seen in FIG. 30.

In another embodiment shown in FIGS. 29-31 extension 306 is not integral with or fixed to airway 302, but includes a swivel retainer 322 fitted into extension 306, which retainer 322 retains collapsible airway 304 on extension 306. Extension 306 continues to be press fit into receiving structure 52 as described and shown above. As best seen in the side cross sectional view of FIG. 31, swivel retainer 322 has an upper circumferential flange 332 on each of its prongs 324, which flange 332 is press fit into a mating groove defined behind a corresponding flange 334 extending from the bottom circumferential edge or wall of extension 306. A plurality of such flanges 334 may be provided, e.g. four of which three are seen in FIG. 30. A lip 320 may be integrally formed on the bottom circumferential edge of the wall of extension 306 and notches defined in lip 320 so that the upper horizontally extending portion 326 of each prong 324 is captured between the corresponding flange 334 and mating notche defined in lip 320 of the lower circumferential edge of the wall of extension 306. In this manner swivel retainer 322 is rotationally fixed to extension 306.

The upper portion of airway 304 is integrally provided with a toroidal termination 318 on top the last frustoconical pleat 308 of the bellows formed wall of airway 302. As best shown in FIG. 31 each prong 324 extends around toroidal termination 318 to integrally connect to an underlying ring 336 of swivel retainer 322. Ring 336 is provided with a radially inwardly extending flange 328 that provides a broadly extending interference surface underneath toroidal termination 318. Flanges 328 extending from ring 336 prevent toroidal termination 318 from moving any substantial longitudinal displacement within swivel retainer 322, thereby maintaining an effective air seal between airway 306 and extension 306. On the other hand, toroidal termination 318 and airway 302 with it are nonetheless substantially free to rotate within swivel retainer 322. By this means airway 302 and with it reservoir 40 are free to rotate or swivel with respect to extension 306 and mouthpiece 134 with it.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments. Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. A housing for use as part of a nebulizer apparatus for use with a source of carrier gas flow for providing aerosolized medication to a patient, the housing comprising:

a cylindrical bell cap;

a collar disposed beneath the cylindrical bell cap;

a collapsible airway having two opposing ends;

a removable extension coupled to one of the two opposing ends of the collapsible airway; and a flexible plug defined within a surface of the housing at an angle which is normal to the surface of the housing, the plug comprising a cross sectional cut configured to accommodate direct insertion of a drug dispenser, wherein a first one of the two opposing ends of the collapsible airway is integrally formed with a top surface of the cylindrical bell cap and communicates with an internal volume defined in the cylindrical bell cap, wherein a second one of the two opposing ends of the collapsible airway comprises a toroidal termination configured to couple to a swivel retainer of the extension and communicates the collapsible airway with the nebulizer apparatus, wherein the plug is further communicated directly with the internal volume of the cylindrical bell cap, and wherein the cross sectional cut is configured to close automatically when the drug dispenser is removed.

2. The housing of claim 1 further comprising a radial bore defined in the cylindrical bell cap.

3. The housing of claim 2 wherein the plug is disposed in the radial bore.

4. The housing of claim 1 wherein the collar is configured to be removably coupled to a reservoir.

5. The housing of claim 4 wherein the collar comprises an internal threading configured to engage with the reservoir.

6. The housing of claim 1 wherein the removable extension is configured to be coupled to a mask connector of a face mask.

7. The housing of claim 1 wherein the removable extension is configured to be coupled to a receiving structure of a T-junction.

8. The housing of claim 1 wherein the cylindrical bell cap is integrally formed with the collar.

9. The housing of claim 1 wherein the internal volume of the housing is fluidly communicated with a detachable reservoir.

10. A method for using a housing as part of a nebulizer apparatus for use with a source of carrier gas flow for providing aerosolized medication to a patient, the method comprising:

providing a housing;

coupling an extension to a collapsible airway portion of the housing;

coupling a reservoir to the housing;

inserting a drug dispenser into a flexible plug defined within a surface of the housing at an angle which is normal to the surface of the housing, the plug further being communicated directly with an internal volume of the housing;

filling the reservoir with a medication through the flexible plug; and removing the drug dispenser from the flexible plug, wherein inserting the drug dispenser into the flexible plug comprises inserting, the drug dispenser into a cross sectional cut defined into the flexible plug, wherein removing the drug dispenser from the flexible plug comprises automatically closing the cross sectional cut when the drug dispenser is removed, and wherein coupling the extension to the collapsible airway portion of the housing comprises coupling a toroidal termination of the collapsible airway portion into a swivel retainer disposed on the extension.

11. The method of claim 10 wherein coupling the reservoir to the housing comprises coupling the reservoir to the housing by engaging an internal threading disposed on an inside surface of the housing.

* * * * *